United States Patent
Dunbar (12)

(10) Patent No.: US 11,357,882 B2
(45) Date of Patent: Jun. 14, 2022

(54) METHOD, APPARATUS AND SYSTEM FOR REDUCING PATHOGENS IN A BREATHABLE AIRSTREAM IN AN ENVIRONMENT

(71) Applicant: TOMPHYZX.LLC, Dundee, NY (US)

(72) Inventor: Thomas Dunbar, Dundee, NY (US)

(73) Assignee: TOMPHYZX.LLC, Dundee, NY (US)

( * ) Notice: Subject to any disclaimer, the term of this patent is extended or adjusted under 35 U.S.C. 154(b) by 0 days.

(21) Appl. No.: 17/401,874

(22) Filed: Aug. 13, 2021

(65) Prior Publication Data

US 2022/0047766 A1 Feb. 17, 2022

Related U.S. Application Data

(60) Provisional application No. 63/221,895, filed on Jul. 14, 2021, provisional application No. 63/150,126, filed on Feb. 17, 2021, provisional application No. 63/113,304, filed on Nov. 13, 2020, provisional application No. 63/065,205, filed on Aug. 13, 2020.

(51) Int. Cl.
| | |
|---|---|
| *A61L 9/20* | (2006.01) |
| *A62B 18/02* | (2006.01) |
| *A62B 18/10* | (2006.01) |

(52) U.S. Cl.
CPC ............. *A61L 9/20* (2013.01); *A62B 18/025* (2013.01); *A62B 18/10* (2013.01); *A61L 2209/111* (2013.01); *A61L 2209/12* (2013.01); *A61L 2209/14* (2013.01); *A61L 2209/16* (2013.01)

(58) Field of Classification Search
CPC .............................. A61L 9/20; A61L 2209/12
See application file for complete search history.

(56) References Cited

U.S. PATENT DOCUMENTS

| 9,480,768 B2 * | 11/2016 | Krosney .................. A61L 9/20 |
|---|---|---|
| 10,473,351 B2 | 11/2019 | Anderson et al. |
| | | (Continued) |

FOREIGN PATENT DOCUMENTS

| EP | 1541179 A1 | 6/2005 |
|---|---|---|
| EP | 1918208 A1 | 5/2008 |
| WO | 2020163733 A1 | 8/2020 |

*Primary Examiner* — Kevin Joyner
(74) *Attorney, Agent, or Firm* — Jodi A. Reynolds, Esq.; Brian B. Shaw, Esq.; Harter Secrest & Emery LLP

(57) ABSTRACT

An air flow system for reducing pathogens in a breathable airstream in an environment has a device having an airstream intake for receiving a volume of untreated air located in a first position, an airstream outlet for expelling a volume of treated air, the airstream outlet located in a second position extending above the first position, a flow path extending between the airstream intake and the airstream outlet, at least one of a UV generator and a UV-C emitter optically coupled to the flow path, a power source operably connected to the one of the at least one of the UV generator and the UV emitter, and a pressure generator fluidly connected to the airstream intake, the pressure generator configured to impart a flow from the airstream intake to the airstream outlet, wherein the pressure generator can be at least one of a force of flow from in line pressurized source or provided by a fan within the housing, and wherein a portion of the flow path includes a UV-C highly reflective surface.

30 Claims, 33 Drawing Sheets

(56) References Cited

U.S. PATENT DOCUMENTS

| | | | |
|---|---|---|---|
| 2008/0152548 A1* | 6/2008 | Clark | A61L 9/205 422/121 |
| 2012/0168641 A1* | 7/2012 | Lizotte | A61L 9/20 250/435 |
| 2014/0158917 A1* | 6/2014 | Stibich | A61L 9/20 250/504 R |

* cited by examiner

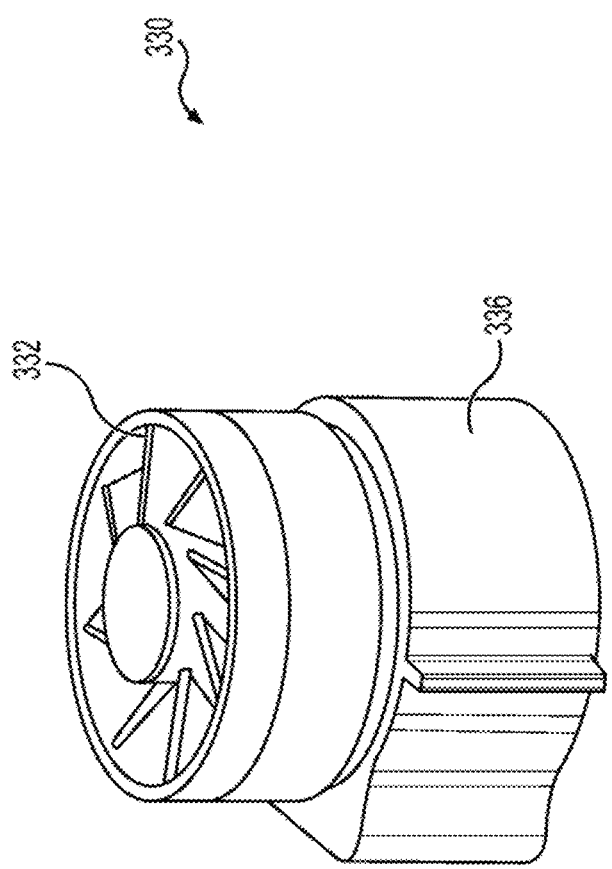

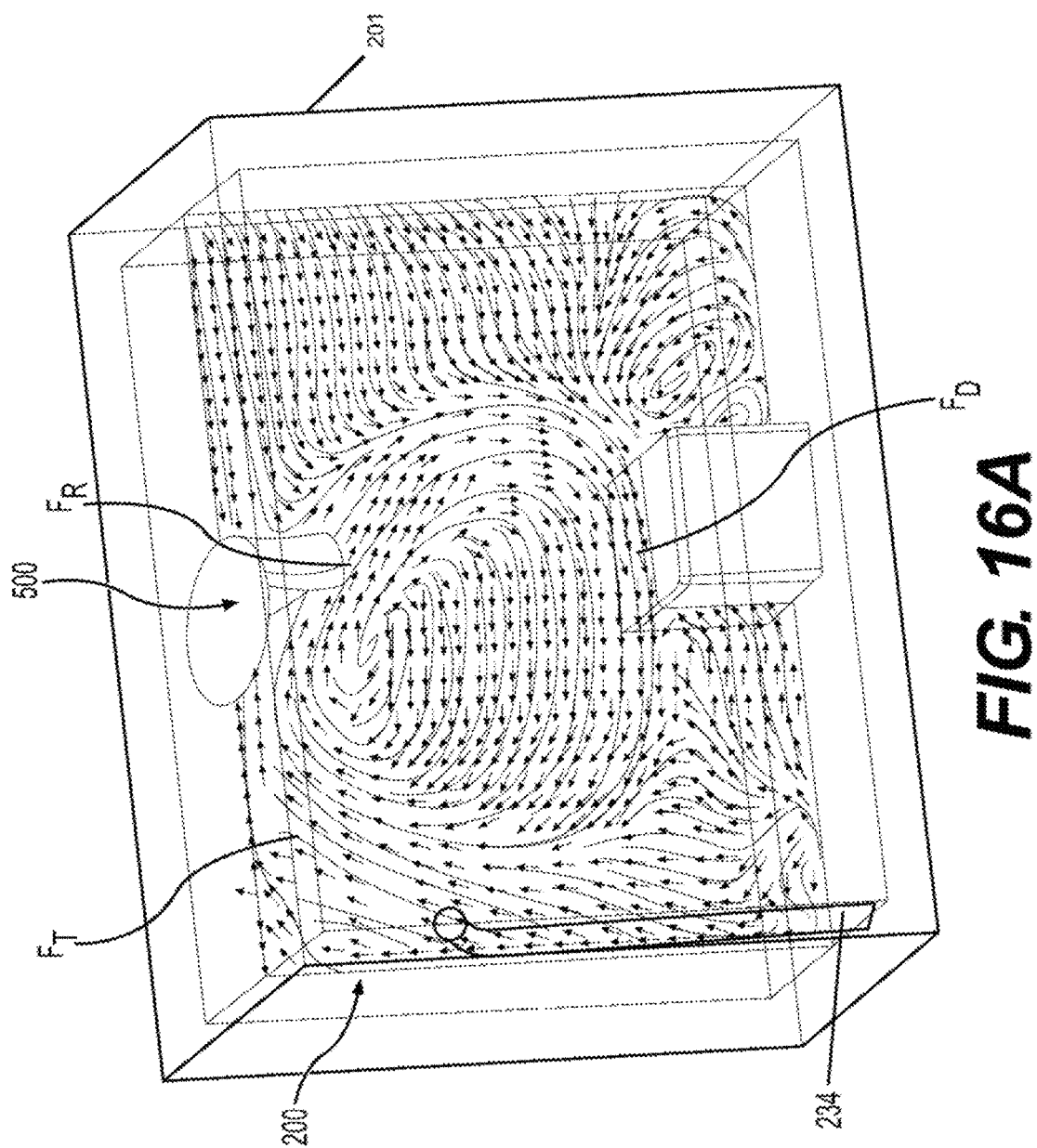

METHOD, APPARATUS AND SYSTEM FOR REDUCING PATHOGENS IN A BREATHABLE AIRSTREAM IN AN ENVIRONMENT

BACKGROUND OF THE INVENTION

Field of the Invention

The present invention relates to pathogen reduction systems, and more particularly, to methods, apparatus and system of reducing pathogens in an airstream through the pathogen reduction system and within an environment.

Description of Related Art

The COVID-19 pandemic is changing the mindset of individuals as the public becomes more aware of the ability to prevent the transmission of communicable diseases. While it was once common to share an untreated airstream with others in an environment, whether enclosed or outside, many individuals are no longer comfortable in such settings. It has been found that mask wearing can greatly reduce the risk of transmitting and contracting COVID-19 and other airborne illnesses. However, many find mask wearing inconvenient or uncomfortable. Further, wearing masks in certain settings is not practical. For example, in a restaurant, individuals cannot eat and wear a mask simultaneously. Further, while one could choose to wear a mask when they are experiencing cold-like symptoms that could be indicative of a COVID-19 infection, such as a runny nose, cough, congestion, and headache, some infective individuals may be asymptomatic or presymptomatic. Thus, they may choose not to wear a mask even though they are unknowingly shedding virus. Thus, it is desired to provide a system that can reduce the risk of COVID-19 exposure without requiring masking.

One option is to treat the air in the environment to reduce the pathogens in the airstream. Exposure of the airstream to a UV-C source, as measured in watts of UV-C energy, can provide a pathogen reduction system. A problem with existing pathogen reduction systems, however, is that they have limited sized illumination cavities and improper pathogen exposure to the UV energy to provide enough treated air in an environment to significantly reduce the pathogens in the environment. Another problem with existing pathogen reduction systems is that they are inefficient and ineffective at killing pathogens.

Further, the amount of UV-C illumination that makes it into the air flow in existing systems is too low. Existing systems specifications describe an illumination value that is defined in terms of watts per $cm^2$ (that is, power per unit area rather than power per unit volume) and not emitted power that passes through the air channel. Thus, the existing system's UV-C power does not provide adequate pathogen reduction for large scale applications. The present system improves upon existing systems.

BRIEF SUMMARY OF THE INVENTION

Embodiments of the present disclosure provide an airflow system for reducing pathogens in a breathable airstream in an environment.

According to one aspect of the present disclosure, there is provided an airflow system for reducing pathogens in a breathable airstream in an environment, the system comprising an air flow system for reducing pathogens in a breathable airstream in an environment, the system comprising a device having an airstream intake for receiving a volume of untreated air located in a first position, an airstream outlet for expelling a volume of treated air, the airstream outlet located in a second position extending above the first position, a flow path extending between the airstream intake and the airstream outlet, at least one of a UV generator and a UV-C emitter optically coupled to the flow path, a power source operably connected to the one of the at least one of the UV generator and the UV emitter, and a pressure generator fluidly connected to the airstream intake, the pressure generator configured to impart a flow from the airstream intake to the airstream outlet, wherein the pressure generator can be at least one of a force of flow from in line pressurized source or provided by a fan within the housing, and wherein a portion of the flow path includes a UV-C highly reflective surface that increases the power contained within the illumination chamber well above the power emitted from the UV generator.

According to another aspect of the present invention, an apparatus for presenting treated air comprises an elongate housing extending along a longitudinal axis, the elongate housing defining (i) an air intake extending along the longitudinal axis and located in a predetermined position, (ii) an air output port extending along the longitudinal axis and located above the predetermined position of the air intake, and (iii) an illumination channel having a UV-C highly reflective surface and extending along the longitudinal axis, wherein the illumination channel is fluidly connected to the air intake and the air output port, a pressure generator fluidly connected to the airstream intake and the air output port, the pressure generator configured to impart a flow from the air intake to the air output port, and a UV-C source within the illumination channel, wherein untreated air flows from the air intake, into the illumination channel, and then flows out of the air output port as treated in a first substantially horizontal direction followed by a second substantially downward direction.

BRIEF DESCRIPTION OF THE SEVERAL VIEWS OF THE DRAWING(S)

FIG. 9 is a perspective view of a light blocking fan for use in practicing exemplary embodiments of this disclosure;

FIG. 16A is a perspective view of a room having an airflow deflector fluidly coupled to an airflow pathogen reduction device suitable for use in practicing exemplary embodiments of this disclosure;

DETAILED DESCRIPTION OF THE INVENTION

Figure 1A:
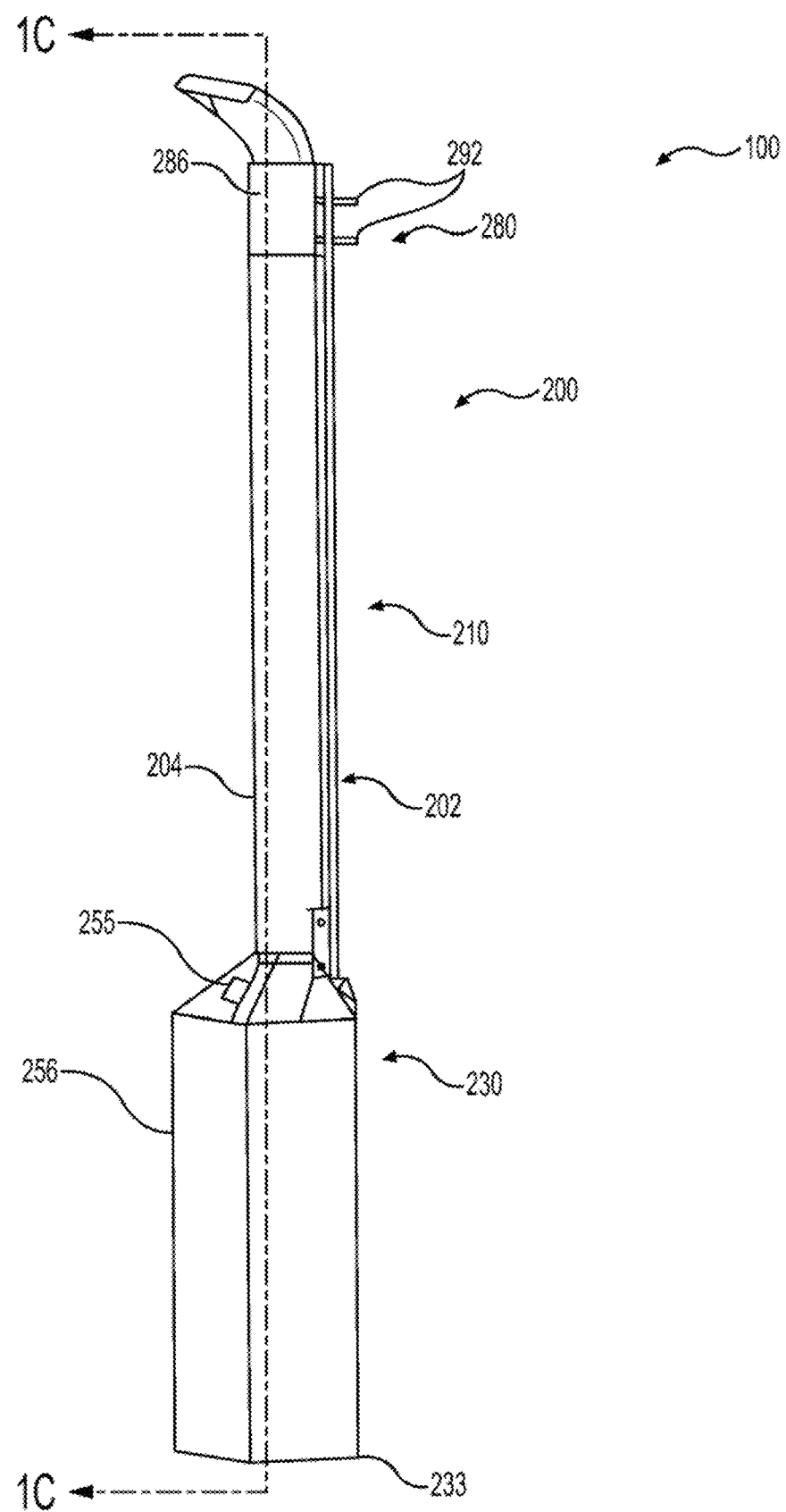
FIG. 1A is a perspective view of an airflow pathogen reduction system suitable for use in practicing exemplary embodiments of this disclosure.
Figures 1B, 1C:
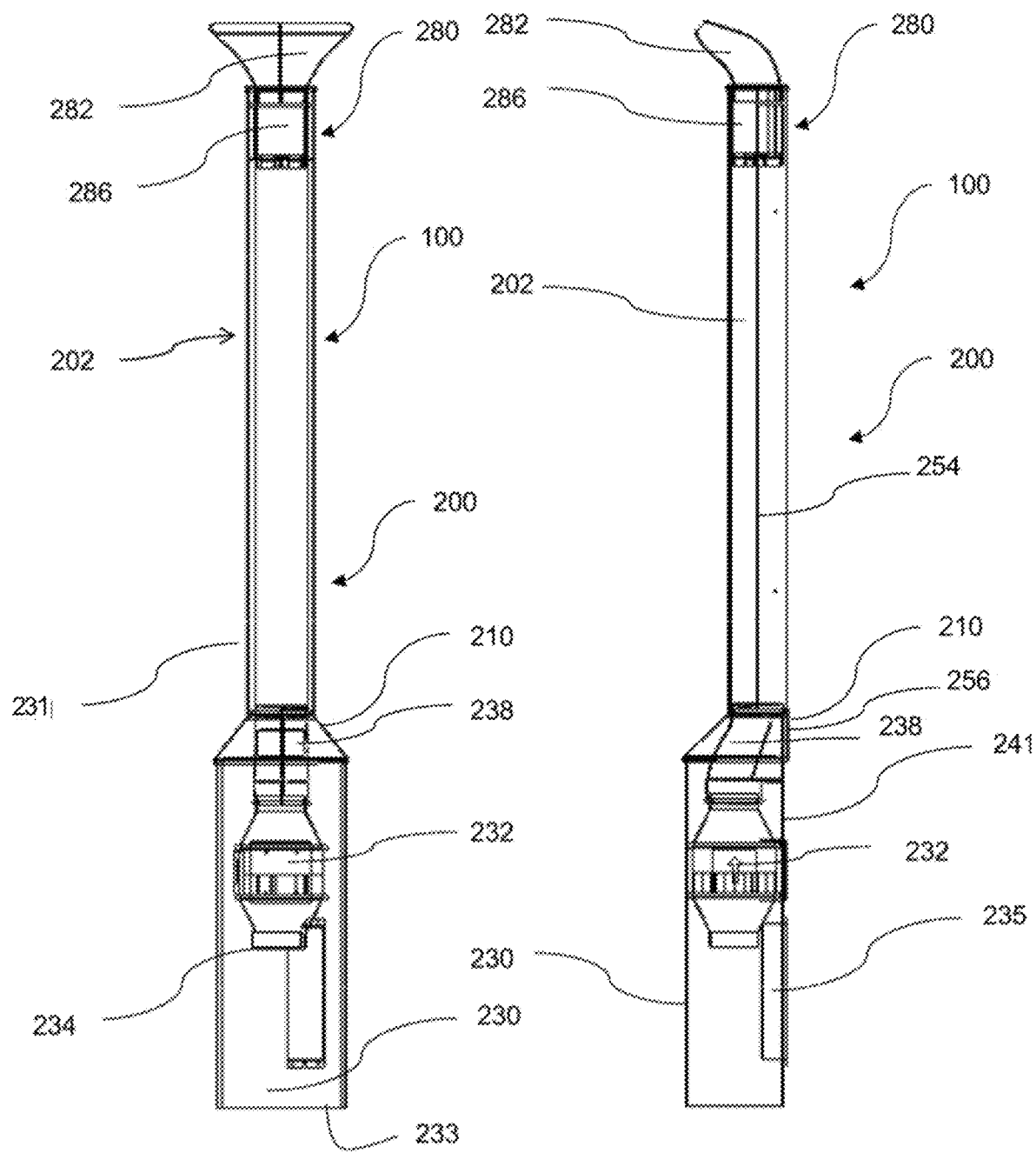
FIG. 1B is a front view of the airflow pathogen reduction system of FIG. 1A suitable for practicing exemplary embodiments of this disclosure having a panel portion of a lower housing removed to show the interior, a portion of a fan housing removed to show a fan within the lower housing, and a portion of an illumination chamber removed to show the chassis and frame.
FIG. 1C is a cross-sectional view of the airflow pathogen reduction system of FIG. 1A taken along lines 1C-1C, suitable for practicing exemplary embodiments of this disclosure.

It is to be understood that the invention may assume various alternative orientations and step sequences, except where expressly specified to the contrary. It is also to be understood that the specific assemblies and systems illustrated in the attached drawings and described in the following specification are simply exemplary embodiments of the inventive concepts defined herein. Hence, specific dimensions, directions, or other physical characteristics relating to the embodiments disclosed are not to be considered as limiting, unless expressly stated otherwise. Also, although they may not be, like elements in various embodiments described herein may be commonly referred to with like reference numerals within this section of the application.

Referring to FIGS. 1A-8, an airflow pathogen reduction system 100 and certain components thereof are shown. For purposes of the present description, the airflow pathogen reduction system 100 is set forth as an individual airflow pathogen reduction device 200. However, it is understood, the disclosure is not limited to the airflow pathogen reduction device 200 and can be included as one of a plurality of airflow pathogen reduction devices 200. Further, such plurality of airflow pathogen reduction devices 200 can be in communication with each other and/or in communication with a processor as described in more detail below. Further, the airflow pathogen reduction system 100, including at least one airflow pathogen reduction device 200 can be incorporated into an HVAC or other type of heating, ventilation, and/or air-conditioning system. The term airflow pathogen reduction system 100 can encompass any device capable of killing pathogens in an airflow and embodiments of the present invention are not limited to the particular configuration of airflow pathogen reduction system 100 or device 200. By pathogen, it is meant any virus, bacteria or other disease-causing microorganism.

The airflow pathogen reduction device 200 provides pathogen reduction in an environment, such as a room, enclosed space or non-enclosed predetermined area. The airflow pathogen reduction device 200 includes an illumination chamber 202. In one exemplary embodiment, the illumination chamber 202 is a "single pass" exposure chamber having a single pass illumination channel defined by an elongated housing 204. The elongate housing 204 enables a maximum cross section and linear length for the exposure chamber and therefore less resistive force on the air flow through the device 200. The illumination chamber 202 includes a highly reflective layer 206 and a UV-C radiation source 208. In an exemplary embodiment, the layer 206 is a lining or coating having a reflectance in the range of 85%-97%, and more preferable, approximately 90%-97% and even more preferably approximately 97%. In one exemplary embodiment, the illumination chamber 202 includes a layer of anodized aluminum creating a mirror-like surface and providing approximately 90% reflectance. In another exemplary embodiment, the lining is a Teflon based diffuse reflective layer providing a reflectance of up to 97%. In yet another exemplary embodiment, the layer 206 is a specialized coating that provides a reflectance of up to 97%. Such lining can include a UV-C reflectance sheet from Porex Filtration Group that reflects 97% of UV-C light. Multi-layers of coatings or linings may further be provided. The interior of the illumination chamber 202 with a highly UV-C reflective material will increase the effective optical power or multiplier, as discussed below. The coating or lining, in one exemplary embodiment is transparent to other types of radiation, including VIS radiation, UV-A radiation and UV-B radiation. The illumination chamber 202 further includes UV-C radiation source 208 as a UV generator or UV emitter. The UV-C source 208, in one exemplary embodiment is at least one LED. In another exemplary embodiment, the UV-C source 208 is an elongated bulb or lamp arranged parallel to the flow direction of the air. For example, the UV-C, in an embodiment is a standard low-pressure mercury vapor lamp. The UV-C source 208 may alternatively include an excimer lamp or a pulse xenon lamp. For example, the Larson Electronics Far UV 222 nm, 150 W Excimer Lamp, commercially available at www.larsonelectronics.com, may be used. Such an excimer lamp utilizes Krypton Chloride (KrCl) to provide 222 nm UV-C light. In yet another exemplary embodiment, the UV-C source is a pulsed Xenon lamp. A Xenon UVC lamp provides a wide spectrum of wavelengths instead of a single wavelength. This wider spectrum of wavelengths (starting at 170 nm) provides a broader antimicrobial effect, which means they have the ability to inactivate more pathogens. An example of a Xenon UVC lamp that can be used is Ushio 5000262, UPX-44 Pulse Xenon Lamp, commercially available at www.ushio.com.

In one exemplary embodiment, the airflow pathogen reduction device 200 includes a middle enclosure 210 which includes the illumination chamber 202, a lower enclosure 230, and an upper enclosure 280.

As shown in FIGS. 1A-1C, and 5-7, the middle chamber enclosure 210 includes the elongated housing 204 having a chassis frame 212 for supporting the illumination chamber 202. The chassis frame 212 in one exemplary embodiment is formed to assemble two elongated sections 214, 216 each having outer extensions 217, 218, respectively, and an inner channel 222, 224. The reflective layer is applied to the inner channels 222, 224, then the two elongated sections 214, 216 are secured together to form a tube. For example, a "u" channel or clips 226 and/or a seal (not shown) can be formed along the adjoining outer extensions of the inner channels 222, 224 to the chassis 212. The seal includes, but is not limited to, an adhesive, a sealant, a gasket, or other seal. By "seal," it is meant that elongated sections 214, 216 are at least substantially airtight or impermeable. In an embodiment, the u-channels or clips 226 form a light seal wherein the elongated sections 214, 216 are partially airtight. Alternatively, the reflective layer can be applied to the formed tube after assembly of the inner channels 222, 224. In an exemplary embodiment, the chassis frame 212 can be formed of sheet metal. In another exemplary embodiment, the chassis frame 212 is a supporting frame for a tube providing the illumination chamber 202. Further, the chassis frame 212 may further include a bend 228 in the webs of the chassis frame 212 channel to provide strength, flexibility, and adjustability during assembly. The chassis frame 212 may further include an extension sections 225, 227, each having a length that can be sized according to the diameter of the illumination chamber 202. In an embodiment, the chassis frame 212 also includes a plurality of apertures 229 for receiving fasting bolts, screws, or the like to attach the illumination chamber 202 to the lower chassis 241. Having two elongated sections 214, 216 and u-channels or clips 226 provides the ability to more easily service and clean the illumination chamber 202, as well as exchange the UV-source, as the elongated sections 214, 216 can be separated. In an embodiment, the chassis frame 212 and elongated sections 214, 216 are formed such that the length is easily adjusted and optimized based on the height of the room and other features. This formed profile is used for many exemplary embodiments to transfer the processed air to desired exit distribution locations. Although two elongated halves 214, 216 each having an inner half round channel 222, 224, respectively, is shown, it should be appreciated that other shapes are possible, including but not limited to square or rectangular. Further, it should be appreciated that other proportions are possible as well. For example, the first elongated section 214 may provide one-third of the circumference of the illumination chamber 202 and the second elongated section 216 may provide two-thirds of the circumference of the illumination chamber 202. Further, it should be understood that the airflow pathogen reduction device 200 is not limited to the particular disclosed chassis frame 212. In an exemplary embodiment, elongated section 214 is welded to chassis frame 212.

As shown in FIGS. 1A-3, the lower enclosure 230 can be any of a variety of exemplary embodiments and may include a fan 232 for promoting airflow through the device 200, an air intake 234, and an opening 233 of the lower enclosure 230. In an alternative exemplary embodiment, a fan or airflow promoter is part of a separate system. For example, the airflow promoter may be part of an HVAC System in fluid communication with the device 200. In an embodiment, the air intake 234 is proximate the opening 233 of the lower enclosure 230. In another embodiment, the air intake 234 is spaced from the opening 233. For example, the air intake 234 may be spaced from the opening 233 in a range of approximately 6 inches to 2 feet. The lower enclosure 230 may further include a sound reduction cavity 236, an air transition portion 238, an electronics cavity 240, and a lower lamp support 242. The sound reduction cavity 236 in one exemplary embodiment, includes sound reducing foam to reduce the noise of the fan 232. The lower enclosure 230 can include various sensors and electrical connections to the UV-source 208 and sensors 244. In certain embodiments, the lower enclosure 230 may further include a filter material either proximate the air intake 234 or proximate either side of the fan 232. In one embodiment, a filter having perforations sized to permit particles below a desired size pass through is provided. For example, a filter may prevent airborne particles between 0.3 and 1.0 micrometers in diameter to pass. In another embodiment a high efficiency particulate air (HEPA) filter is used.

Figure 2:
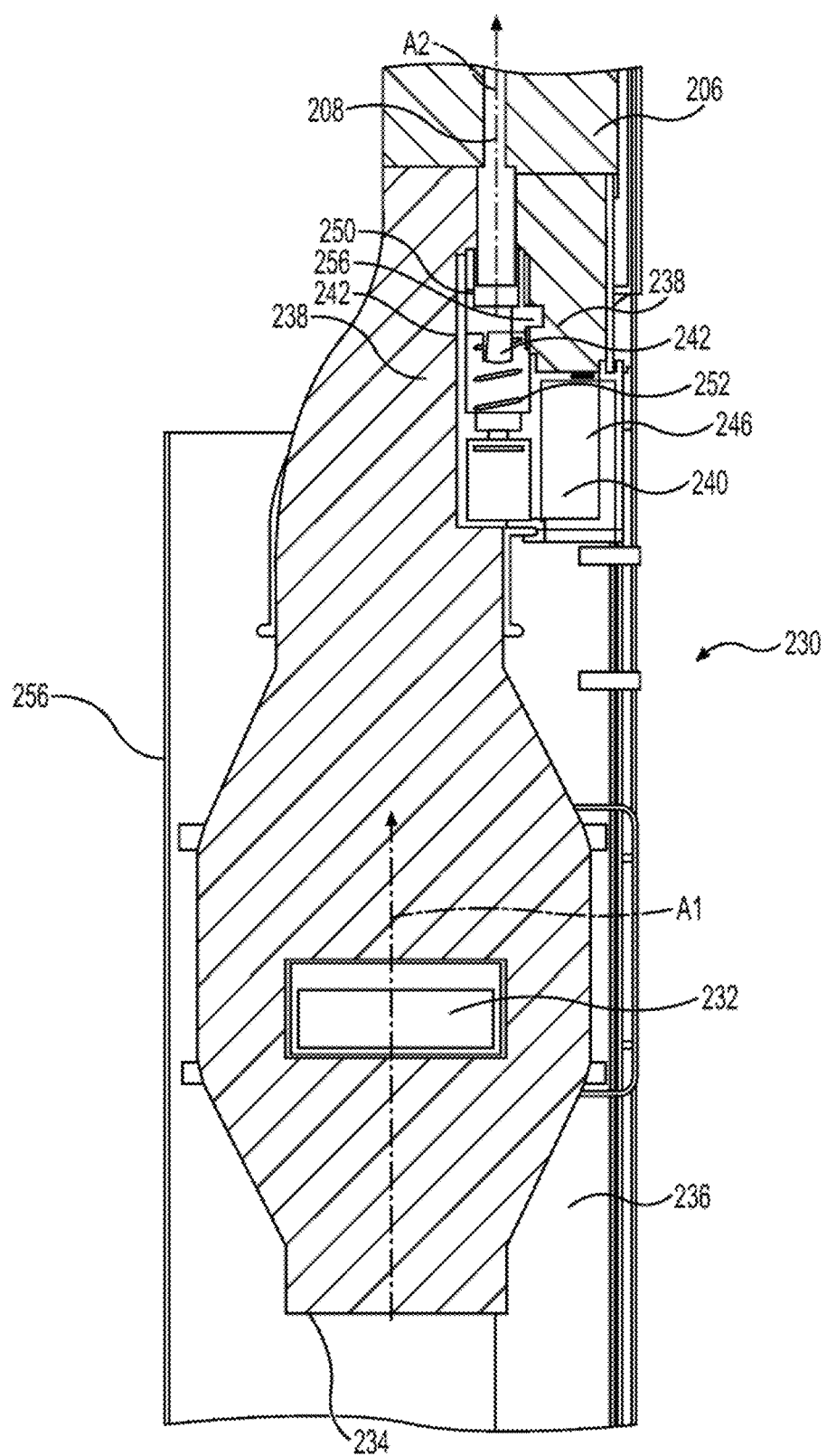
FIG. 2 is side section view of a portion of the airflow pathogen reduction system of FIG. 1 suitable for use in practicing exemplary embodiments of this disclosure.
Figure 3:
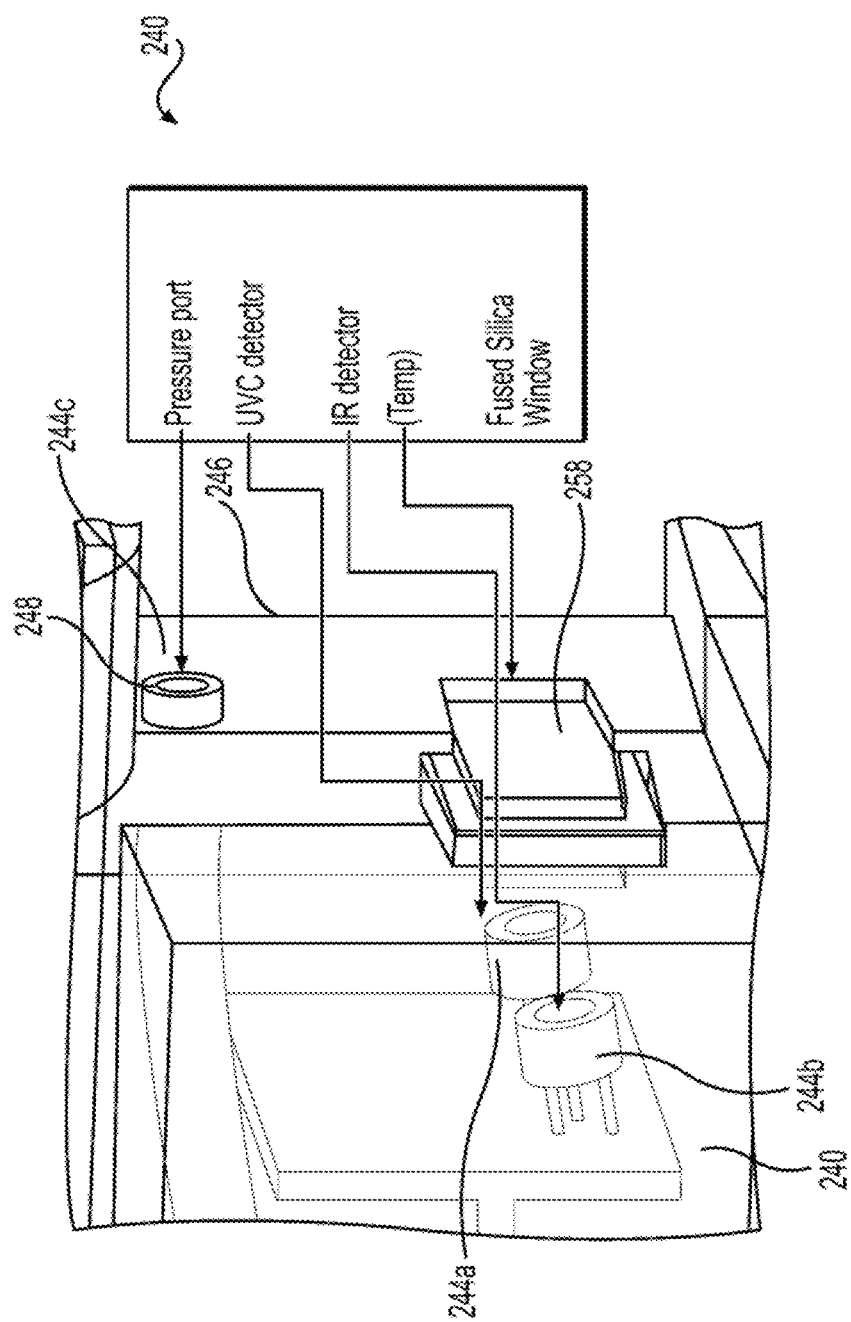
FIG. 3 is a perspective view of a portion of the sensor cavity of the airflow pathogen reduction system of FIG. 1 suitable for use in practicing exemplary embodiments of this disclosure.
Figure 4:
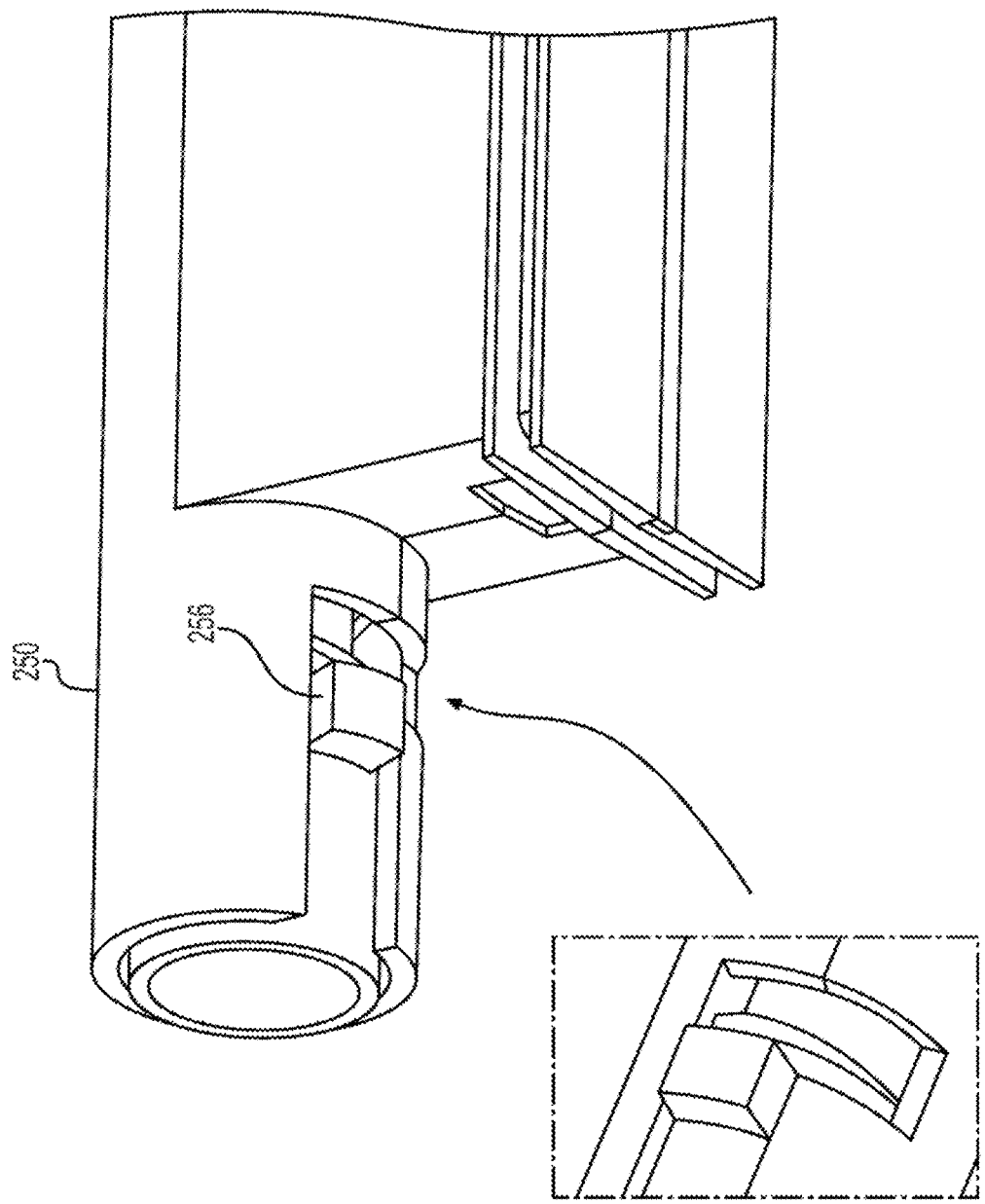
FIG. 4 is a perspective view of a release mechanism of the lamp electrical connector assembly of the airflow pathogen reduction system of FIG. 1 suitable for use in practicing exemplary embodiments of this disclosure.
Figure 5:
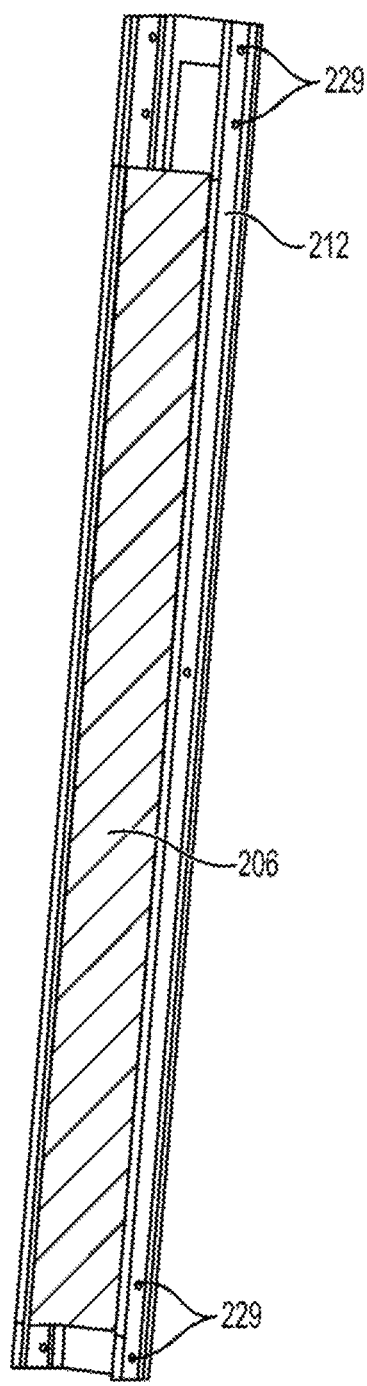
FIG. 5 is a partial top perspective view of an illumination chamber of the airflow pathogen reduction system of FIG. 1A showing a half-portion of the highly reflective UV-C surface and chassis frame, suitable for use in practicing exemplary embodiments of this disclosure.
Figure 6:
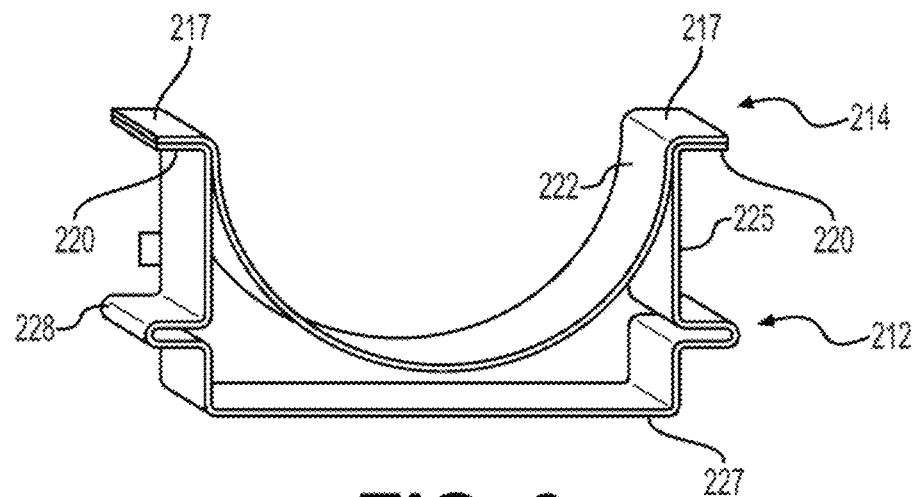
FIG. 6 is a perspective view of a half-portion of a chassis having a reflective surface and chassis frame of the illumination chamber of FIG. 5 suitable for use in practicing exemplary embodiments of this disclosure.
Figure 7:
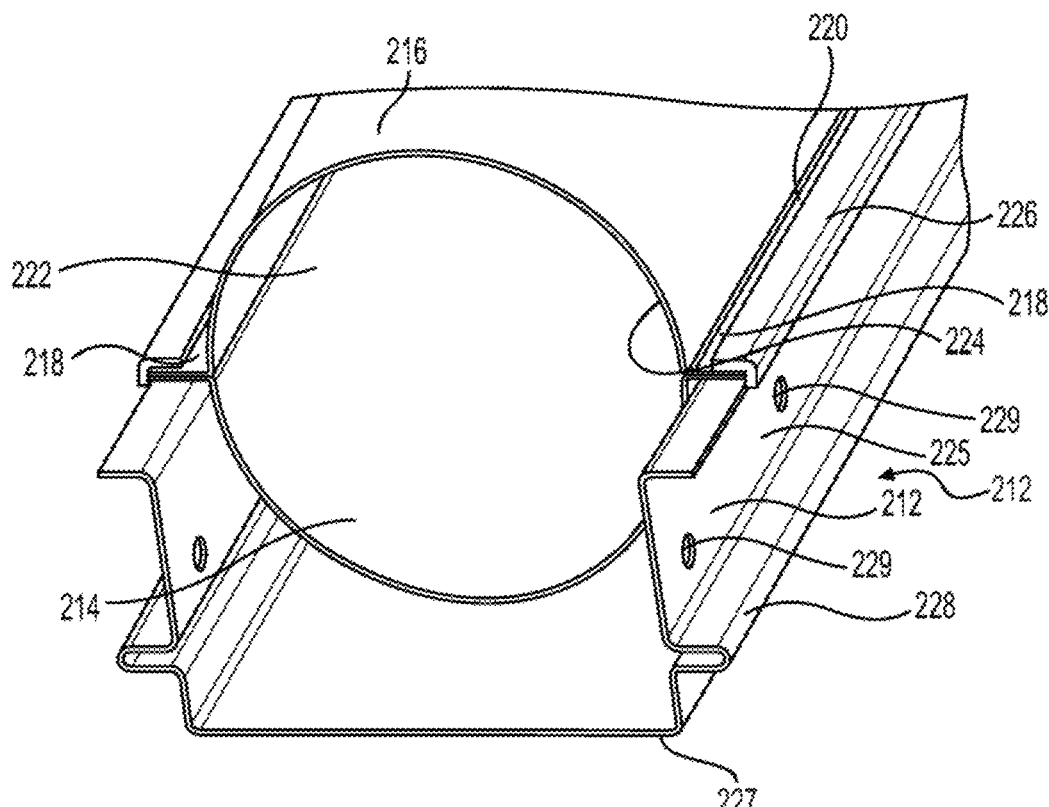
FIG. 7 is a perspective view of an enclosed portion of the chassis and the chassis frame of the illumination chamber shown in FIG. 6 suitable for use in practicing exemplary embodiments of this disclosure, the enclosed portion formed by at least partially sealing two half-portions of the chassis together.
Figure 8:
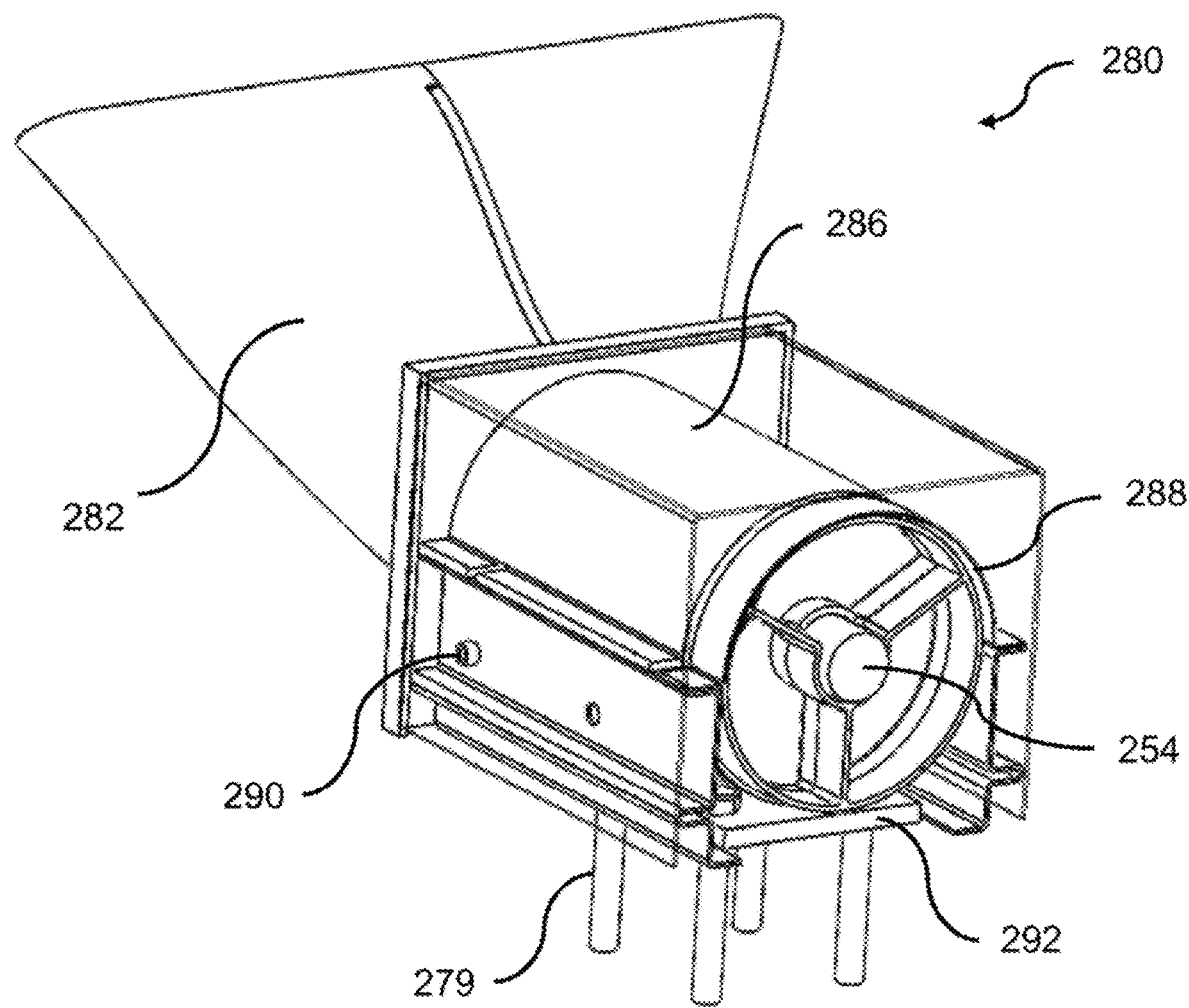
FIG. 8 is a perspective view of an upper enclosure portion of the airflow pathogen reduction system of FIG. 1 viewed from the bottom which is suitable for use in practicing exemplary embodiments of this disclosure.

As shown in FIG. 2, the air transition portion 238 is configured to bring the air from an axis $A_1$ of the fan 232 axis down to the illumination cavity axis $A_2$ allowing a reduced volume of the illumination chamber 202 and volume of the overall device 200. As shown in FIG. 3, the sensors 244 can include, but are not limited to, a UV-C monitor sensor 244a for detecting the UV-C light within the illumination chamber 202 and an IR radiation sensor 244b for measuring a temperature of the illumination chamber 202. In one embodiment, the UV-C source 208 is turned off if a temperature within the illumination chamber 202 exceeds safe levels as determined by certification of the embodiment design by applicable industry standards such as UL, FDA and the Department of Defense. It should be appreciated, however, that other sensors may be included. In one exemplary embodiment, the sensors are protected behind an optical window 258. For example, the sensors 244 can be within an enclosed housing 246 having a fused silica window proximate the illumination chamber 202. A pressure sensor 244c for detecting a change in pressure between the illumination chamber 202 and the lower enclosure 230 as a measure of flow is provided on the circuit board (see FIG. 21). The pressure sensor 244c includes a pressure port 248 extending beyond the enclosure housing 246 into the illumination chamber 202. Although the sensors 244 are shown as part of the lower enclosure 230, it is possible to have the sensors 244 included instead, or additionally, in other portions of the device 200 and these modifications are intended to be included within the scope of the invention as claimed. The lower enclosure 230 can further include a lamp electrical connector assembly 250 as shown in FIG. 2. The lamp electrical connector assembly 250 includes, in one exemplary embodiment, a bias spring 252 to secure a UV-C lamp 254 having an electrical connection power between 50 W and 800 W, and more preferably between 75 W and 200 W. The lamp electrical connector assembly 250 further includes, in certain exemplary embodiments, a lock 256, for example as shown in FIG. 4, for securing in a locked position the bias spring 252 and therefore, the lamp 254, when loaded and for releasing the bias spring 252 when in an unlocked position. As shown in FIGS. 1 and 2, the lower enclosure 230 may include an outer housing 256 for containing or concealing the fan 232, air intake 234, lamp electrical connector assembly 250, housing 246, and other components. The lower enclosure 230 may further include a user interface 255, input and display as further described below. It should be appreciated, however, that the user interface 255 may be included on other portions of the device 200 or as a separate feature, for example as a wall-mounted device, computer, or mobile device, and these modifications are intended to be included within the scope of the invention as claimed. For example, the device 200 may communicate with other electronic devices including, but not limited to communication technologies of LoRaWAN, Wifi, Bluetooth, M2M, cellular, Narrow Band IoT, and Azure.

Turning now to FIGS. 1A, 1B, 1C and 8, upper enclosure 280 in one exemplary embodiment includes an outlet or air lens 282 to distribute the outflow of the air having reduced pathogens into the room and an inner housing 286. In an embodiment, the outlet or air lens 282 distributes the outflow of the air into a desired location. Such desired location may be the expected position of an individual or individuals, an object in the room, such as a table or chair, or an air deflector (as described below). The upper enclosure 280 further includes a lamp support 288 for supporting an end of lamp 254. In one exemplary embodiment, the upper enclosure 280 includes extrusion piping 286 within the outer housing 280 to provide an interface with an air lens 282. Although the interface between the air lens 282 and extrusion piping 286 is shown as round-to-round, it should be appreciated that other interfaces are possible, including, but not limited to, rectangle-to-rectangle, square-to-square, etc. The extrusion piping 286 in one exemplary embodiment is made from the material KYNAR 740, which is UL VO flame resistant, UV-C resistant, and has <4% UVC reflectivity to reduce light reflections from the illumination cavity to the air exit port through the air lens 286. Extrusion piping 286 length can be adjusted for different applications. The extrusion piping 286 may further include a clamping type opening for engaging a protrusion on the air lens 282 to secure or lock the air lens 282 in place. Threaded mount 290 provides access for a fastener to constrict the clamp in locking the lens 282 and extrusion piping 286 to the upper chassis. The upper enclosure 280 can further include a bracket 292 for mounting to a wall or other support system using fasteners 279. This enables the device to securely hang to the wall of a room. In some exemplary embodiments, the upper enclosure 280, lower enclosure, 230 and middle enclosure 210 include a flat profile for resting against the wall where the device 200 is installed. In another exemplary embodiment, the device is self-standing, or secured to another support structure, including, but not limited to a table, as described in further detail below.

Shorter-wavelength, higher-energy UV radiation of UV-C light is strongly absorbed by most organic materials which makes it suitable for disinfecting and sanitizing applications. Exposure to UVC radiation by humans, however, is considered harmful, and may cause severe skin burns and photokeratitis (eye tissue injuries). To avoid direct skin exposure to UVC radiation, the pathogen reduction apparatus can contain the high intensity UV-C light within the illumination chamber and be prevented from reflecting along the air path to the outside environment.

Turning now to FIG. 9, the airflow pathogen reduction device 200, in an exemplary embodiment can include a light block which can reduce or eliminate UV-C light from escaping the illumination chamber 200 and exiting into an occupied space or volume of air. In one embodiment, the light block is a light blocking fan 330 which is optically opaque while allowing air to pass as it spins. The light blocking fan 330 includes a turbine 332 configured to freely spin without power to let air out of the device 200 while reflecting UV-C light back into the device 200. In another embodiment, the fan can be powered to enhance the system cfm throughput. In one embodiment, the light blocking fan 330 is mounted on the top end of the illumination chamber 202. For example, the light blocking fan 330 may include a cap 336 for engaging the top end of the illumination chamber 200. The light block allows the air to escape but reflects light back in and prevents any direct light out. The cap 336 and turbine 332 can be assembled using a low friction bearing (not shown) to allow the turbine 332 to spin while creating a very small resistance to the overall air flow through the system. The light block fan 330 may further include a reflective coating. The "underside" of the blocking fins of the turbine 332 can be coated with a highly reflective coating thereby increasing the photon density within the chamber for an improvement in pathogen reduction. The light blocking fan 330 provides that there are no straight through paths for light to escape. In one exemplary embodiment, the light blocking fan 330 is positioned at the top or the bottom of the illumination chamber. In another exemplary embodiment, the light blocking fan 330 is positioned at the top and the bottom of the illumination chamber. The light blocking fan 330 blocks the light for exiting the bottom and from exiting the top. Components outside the illumination chamber 200 are omitted for clarity.

In one embodiment, the device 200 is approximately 6 feet in length. In another embodiment, the device is approximately 7 feet in length. However, it should be appreciated that the length of the device 200 can be varied to accommodate different applications. For example, the device 200 may range from approximately 4 feet to approximately 10 feet.

Figure 10A:
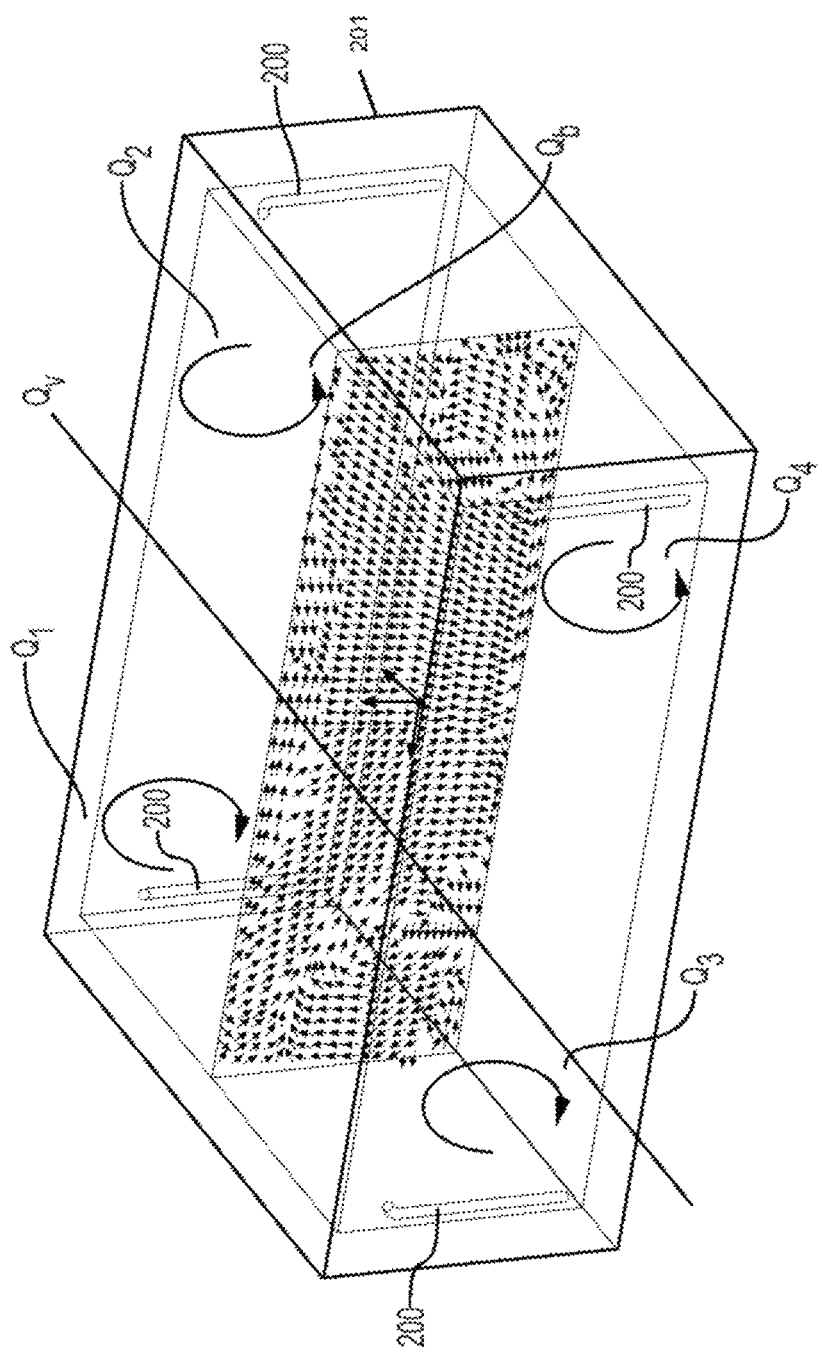
FIG. 10A is a perspective view of a cut plot of a room taken along the long central plane showing the fluid dynamics of a room having four airflow pathogen reduction devices, each disposed at a predetermined distance from the others suitable for use in practicing exemplary embodiments of this disclosure.
Figure 10B:
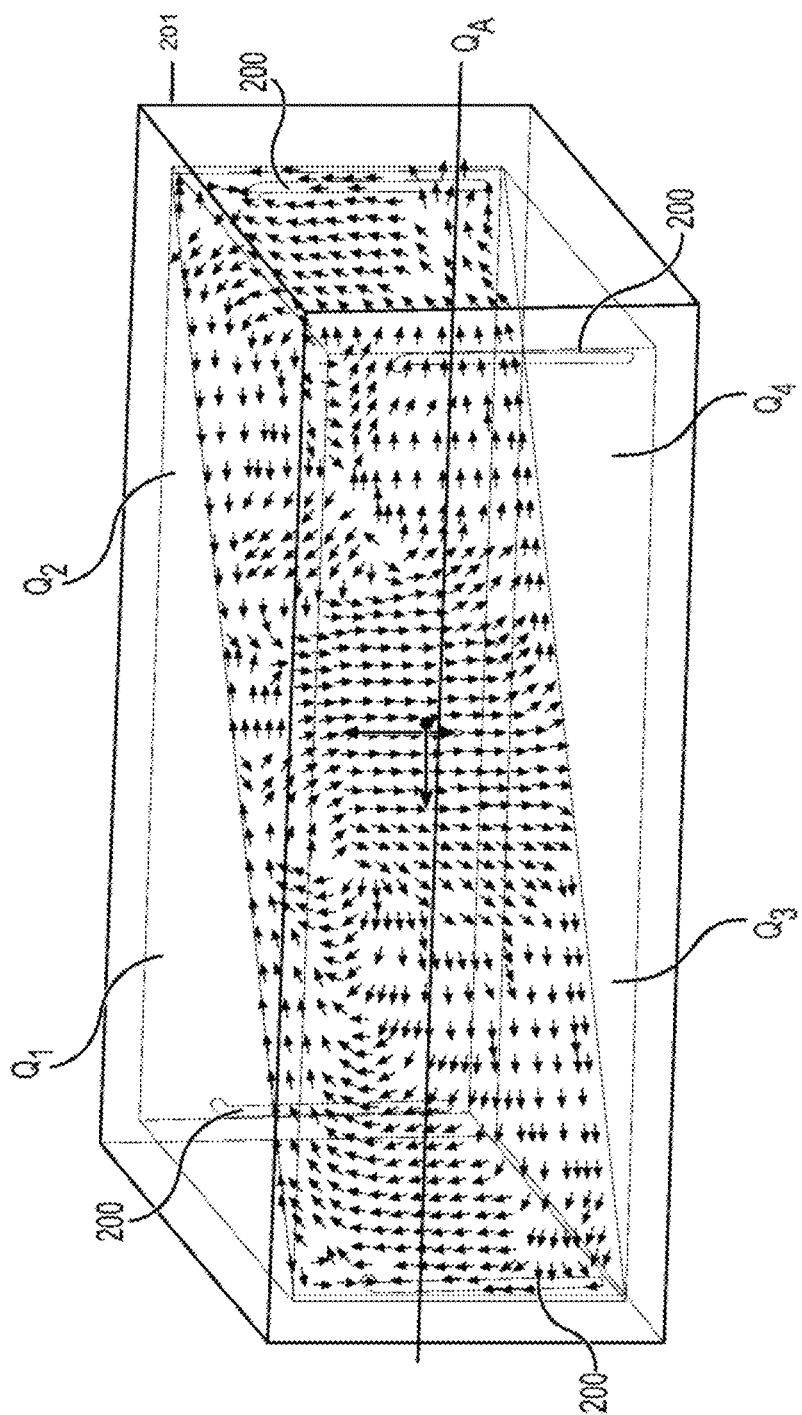
FIG. 10B is a perspective view of a room taken along the diagonal showing the fluid dynamics of a room having four airflow pathogen reduction devices, each disposed at a predetermined distance from the others suitable for use in practicing exemplary embodiments of this disclosure.
Figure 11:
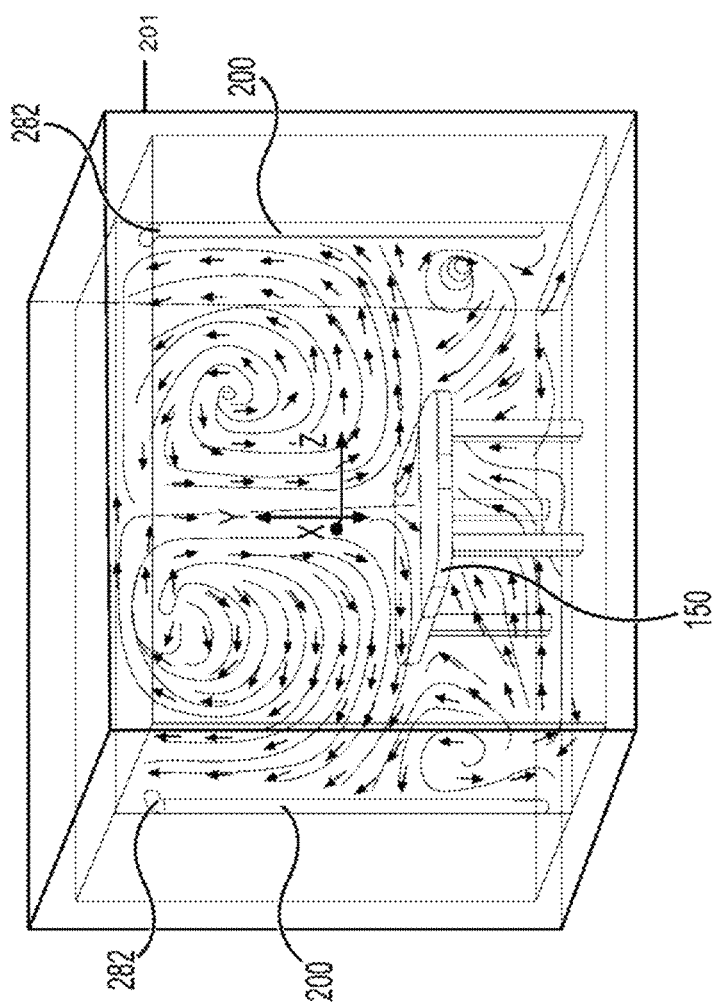
FIG. 11 is a perspective view of a room showing the fluid dynamics of a room having two airflow pathogen reduction devices, each disposed at a predetermined distance from the others suitable for use in practicing exemplary embodiments of this disclosure.

Turning now to FIGS. 10A-10B and 11, shown are cut plots of flow modeling of fluid dynamics of a room having a plurality of devices in the room 201. In FIGS. 10A-B, four devices 200 are positioned in each corner of a 24 ft.×32 ft. room 201 having a ceiling height of 11 feet. Although the four devices 200 are shown in the corners of the room 201, it should be appreciated that the four devices 200 may be placed in other predetermined positions and such configurations are intended to be included within the scope of the invention as claimed. Such a room size is consistent with a classroom or training room size. A cut plot is provided on the long central plane showing the direction of the velocity vectors. The air in the room 201 is approximately "quartered" such that the airflow in each quadrant is substantially isolated from the others. For example, as shown in FIGS. 10A and 10B, in one embodiment, a room 201 can be generally quartered into substantially equal parts along horizontal and vertical lines Qv and Qh, respectively, to form $Q_1$, $Q_2$, $Q_3$, and $Q_4$. In addition, there is a generally downward flow of air in the central area of the room 201. Both characteristics are beneficial in the case of an infected individual in one quadrant, for example $Q_1$. Individuals in the other quadrants $Q_2$, $Q_3$, and $Q_4$ will have a lower probability of transmission and the downward flow drives shed virus from the infected individual down to the floor and back into the devices 200 for viral inactivation as they pass through. In other words, in the event an infected individual is positioned in one quarter of the room 20L the generally "quartered" effect and general downward flow of the air in the central area of the room 20, provides a reduction in infection probability for individuals in the other three quarters of the room 201.

FIG. 11 is a cut plot taken approximately through the center of a room 201. Two devices 200 are in a predetermined position in the room 201, which is smaller than the room 201 provided in FIGS. 10A-10B. In one embodiment, the devices 200 are positioned approximately centrally along two, generally oppositely positioned sidewalls. This cut plot in FIG. 11 shows the interaction of the two air lenses 282 creating a generally downward flow to the center of the room 201. Here, a conference table 150 is centrally located in the room 201. The air then "splits" such that that the air flows outward to the sides of the table 150. This creates a separation of the air between persons sitting across from one another. Any discharge from an infected individual is drawn away from the table center and down to the floor for reprocessing through the airflow pathogen reduction system.

Figure 12:
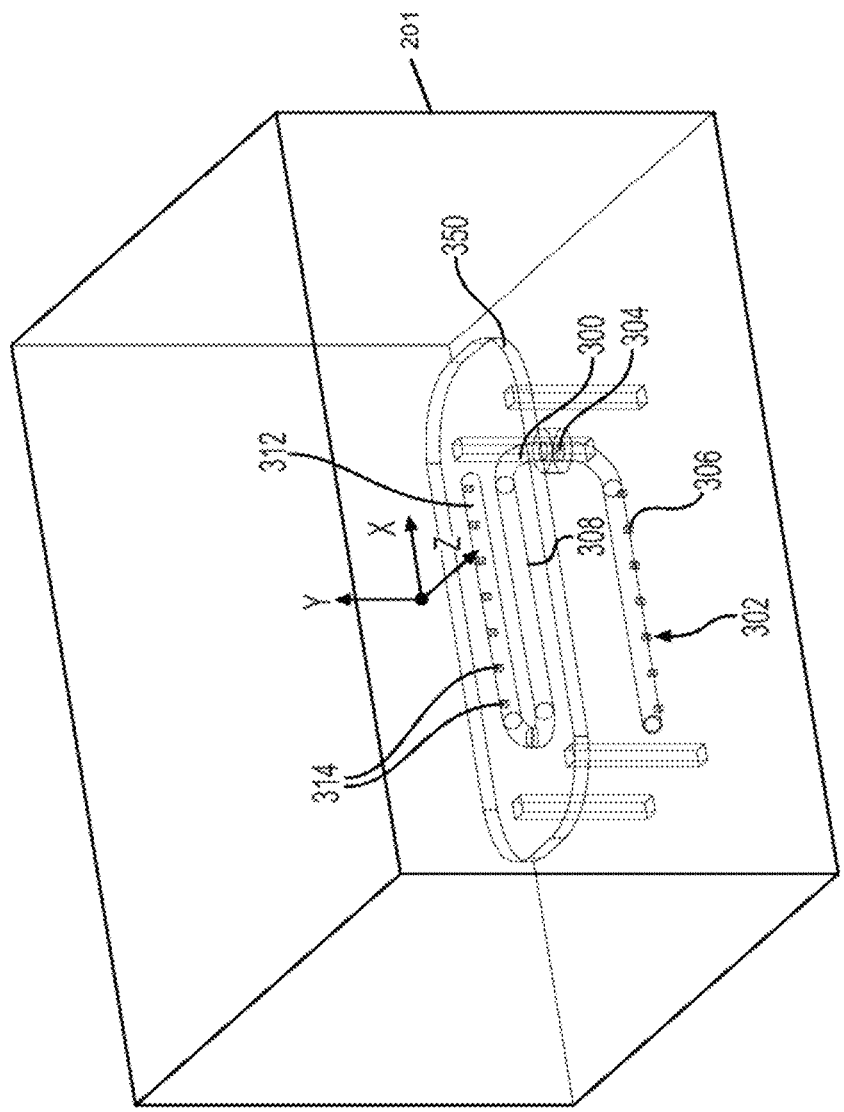
FIG. 12 is a perspective view of an airflow pathogen reduction device incorporated into a table positioned in a room suitable for use in practicing exemplary embodiments of this disclosure.
Figure 13:
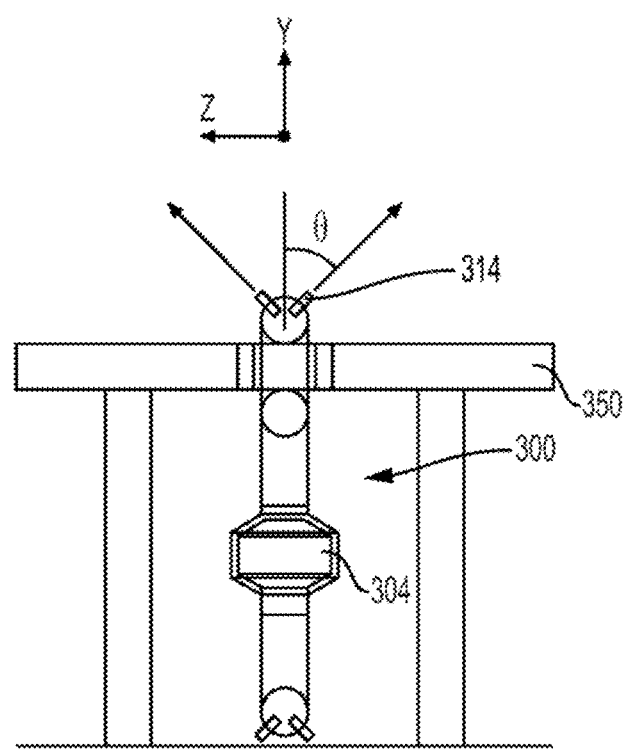
FIG. 13 is a side view of the airflow pathogen reduction device incorporated into the table positioned in the room as shown in FIG. 12 suitable for use in practicing exemplary embodiments of this disclosure.
Figure 14:
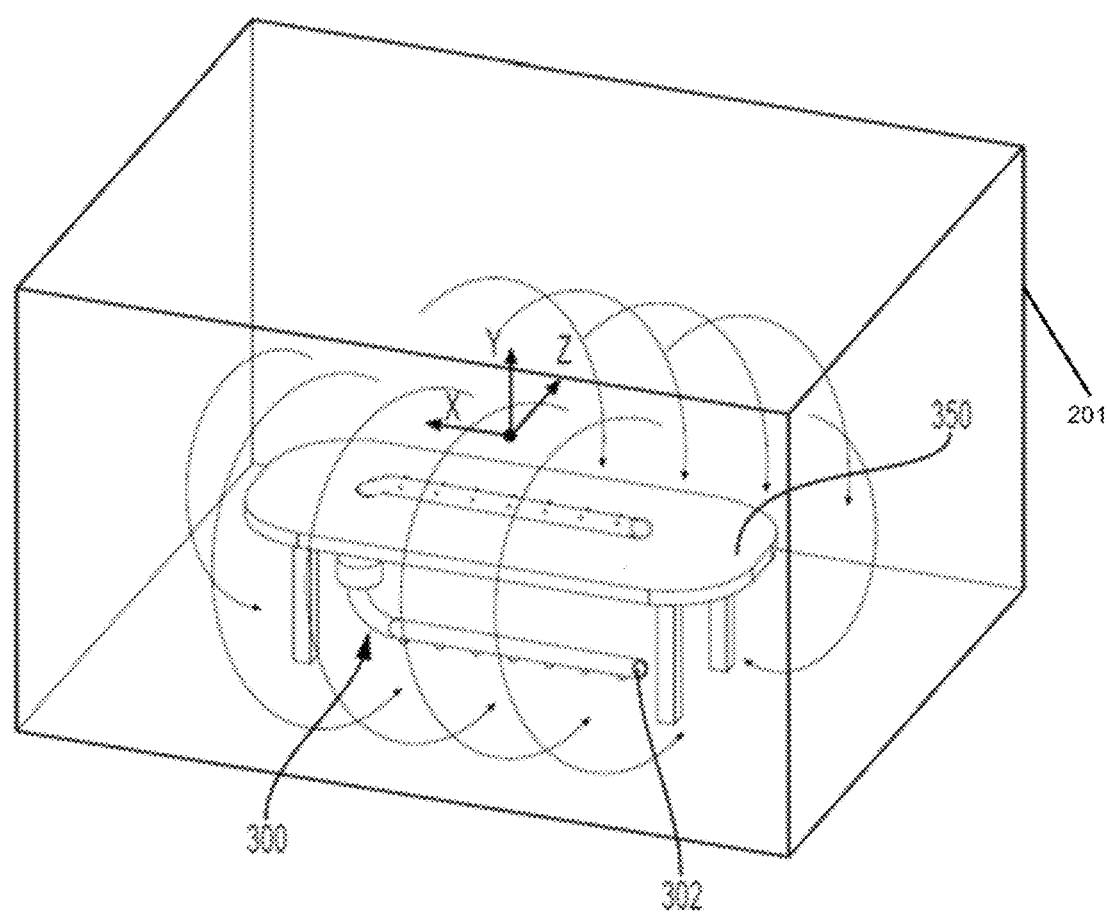
FIG. 14 is a perspective view of an airflow pathogen reduction device incorporated into the table showing a fluid dynamics of the airflow suitable for use in practicing exemplary embodiments of this disclosure.

As shown in FIGS. 12-14, another embodiment includes the device 300 configured as an integral part of table 350.

For example, the pathogen contaminant (viral and bacterial) aerosol concentration shed by an infected individual in the room 201 is desired to flow in a downward direction and away from other individuals in the room 201. By included focused output ports 314 as part of the device 300, the cleaner air is focused at specific targeted areas within a room 201. In FIGS. 12 and 14, the room 201 is approximately 12 ft.×16 ft.×9 ft. and the table 350 is approximately 4 ft.×10 ft. However, other dimensions are possible. In this exemplary embodiment, the air flow pattern achieves a stretched "donut" shaped airflow, for example, as shown in FIG. 14, which greatly reduces "shared air" and presents the cleanest air to individuals sitting around the table.

The desired "interior" pathogen reduction system could be configured with at least a portion of the device 300 positioned underneath the table 350. The device 300 includes components similar to device 200 including, but not limited to the sensors, user interface, an illumination chamber, and a UV-C source, as described above. Additionally, the device includes an air intake portion 302 located upstream of a fan 304. The air intake portion 302 includes at least one intake port 306 and may include a plurality of intake ports 306. For example, in one exemplary embodiment, the air intake portion 302 includes 14 intake ports 306. The intake ports 306 may be adjustable. For example, in one exemplary embodiment, each intake port 306 includes a ball and socket joint configured to swivel approximately 45 degrees. An illumination chamber 308 having a highly reflective material as described above is located downstream of the fan 304 and, in one embodiment, is mounted on the underneath side with horizontal orientation. Treated air flows through the illumination chamber 308 to a distribution fixture 312 located on the top of the table 350 and directed at the individuals. The distribution fixture 312 includes at least one air output port 314 configured to direct treated air toward an individual. In one embodiment, the fan 304 within the air treatment portion 308 creates a negative pressure drawing air into the device 300 and forcing treated air out the output ports 314. With a device 300 such as this, the distance required for "social distancing" may be reduced, which provides applications for smaller rooms. In one exemplary embodiment the distribution fixture 312 includes a plurality of air output ports 314 which are adjustable. By adjustable, it is meant that the output ports 314 may be open or closed, for example for occupied or unoccupied seats, respectively, and/or the output ports 314 may be moveable within a 180 degree range in all directions. In an embodiment, each output port 314 may be on a ball and socket joint configured to swivel approximately 45 degrees. The discharge angles can be adjusted based on at least the location of the individuals and the overall size of the room 201. It should be appreciated that the fan 304 in some exemplary embodiments is positioned in the center underneath the table 350. In another exemplary embodiment, the fan 304 is in an off-center location.

Some buildings include drop ceilings for ease of lighting and other electrical and communications services. In certain embodiments air enters the device 200 at the air intake located proximate the floor and flows through an enclosure having at least an upper treated air delivery portion or air lens 282 plumbed into the drop ceiling area. Input power to the device 200 can enter from the top then into the ceiling or out the bottom to a standard wall plug. Additionally, or alternatively, one or more output ports can be positioned along the ceiling to create a similar flow pattern between individuals that are generally sitting around the table or at other locations within a room 201. In one embodiment, each output port is individually adjustable. The device 200 can be included as part of existing forced air distribution systems, utilizing existing ductwork. In another embodiment, the device 200 is a separately installed device with ductwork directing treated air into a predetermined location.

Output ports can be configured in a long single linear discharge device aligned with the major axis of the conference table. Alternatively, an array of ducted discharge ports having various discharge configurations, from a 360° "fan" to individual ports with potentially one port aiming at each typical seat location can be included. In a cafeteria, for example, an array discharge ports could be located in a ceiling which are centered over dining tables that are fixed.

Figure 15:
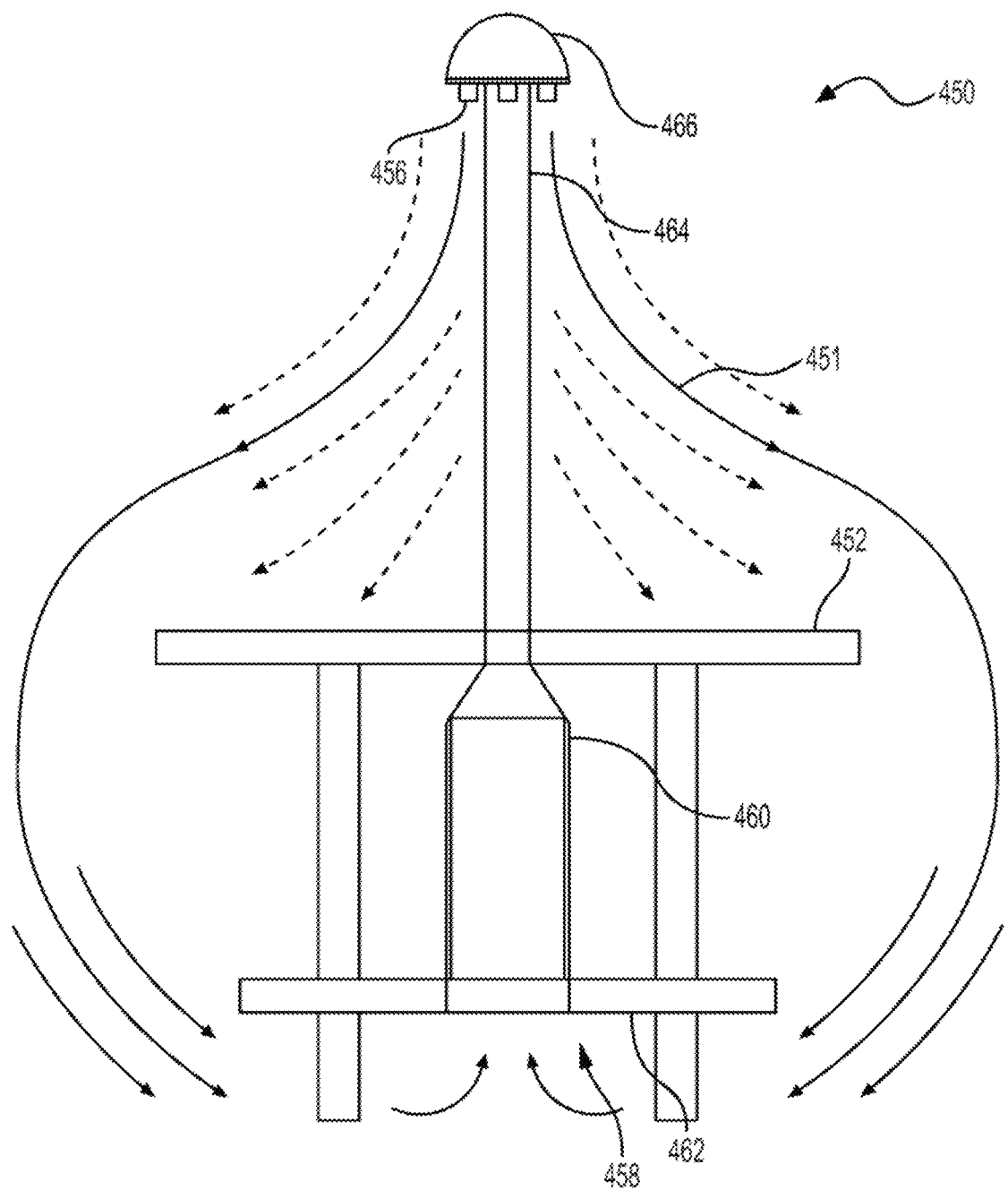
FIG. 15 is a side view of an airflow pathogen reduction device incorporated into a table showing a fluid dynamics of the airflow suitable for use in practicing exemplary embodiments of this disclosure.

FIG. 15 show a "pub" type table airflow pathogen reduction device 450 where localized pathogen-reduction "bubbles" can be obtained. The device 450 includes components similar to device 200 including, but not limited to the sensors, user interface, an illumination chamber, and a UV-C source, as described above. Additionally, the device includes an air intake portion 458 located upstream of a fan within the lower enclosure 460. The air intake portion 458 includes at least one intake port and may include a plurality of intake ports. The intake port(s) may be adjustable. An illumination chamber 464 having a highly reflective material as described above is located downstream of the fan. Treated air flows through the illumination chamber 464 to a distribution fixture 466 located on the top of the table 350 and directed at the individuals. In one embodiment, the device 450 is centrally positioned through a table 452 and generates a conical downward airflow 451. This separates air from all around the device 450 and draws airflow under the footrest 462 to get viral deactivated as it passes back up through. The cleanest air, therefore, is delivered to those seated at the table 452, which is determined by the height of the seats for the configuration application. If anyone at the table is shedding viral particles, the airflow pattern draws the laden air down and away from others at the table. The position of the treated airflow nozzles 456 is adjustable based on height of the table/footrest, and shape of the table. For example, the table, may be designed for 6 individuals so the long axis may have a different distribution nozzle 456 than the short axis. In one exemplary embodiment, the table is approximately four to six feet in diameter and the height of the device is approximately 8 feet. The air intake in one configuration is approximately 0.5 feet from the ground. In an embodiment, table having a four-foot diameter seats approximately four individuals and a table having a six foot diameter seats approximately six individuals. In yet another embodiment, a table having a three-foot diameter seats approximately two individuals. An array of tables 450 can provide isolation between groups of individuals, which is especially important in restaurants and bar-type settings. In an alternative exemplary embodiment, the device 450 is free-standing and proximate a table, rather than positioned through the table.

Figure 16B:
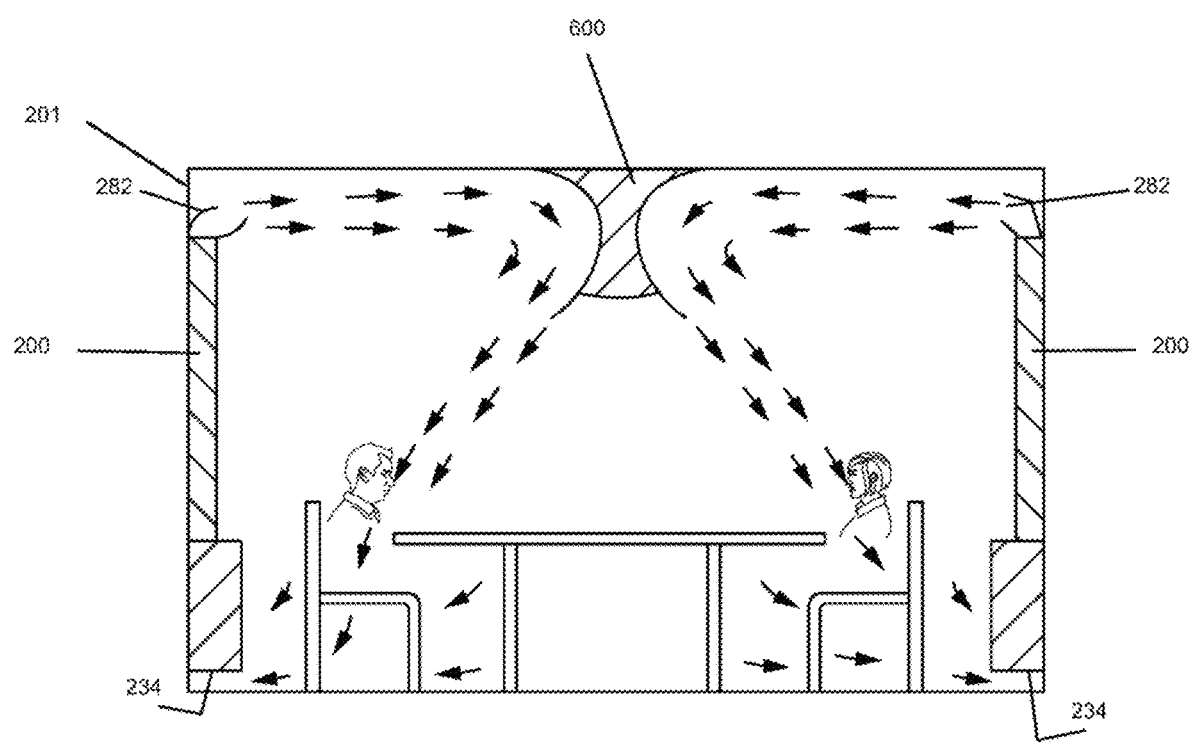
FIG. 16B is a perspective view of a room having an airflow deflector fluidly coupled to a plurality of airflow pathogen reduction devices suitable for use in practicing exemplary embodiments of this disclosure.
Figure 17:
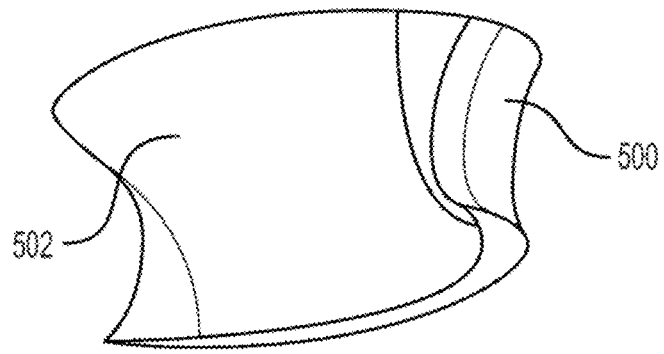
FIG. 17 is a bottom perspective view of the airflow deflector shown in FIG. 16A suitable for use in practicing exemplary embodiments of this disclosure.
Figure 18:
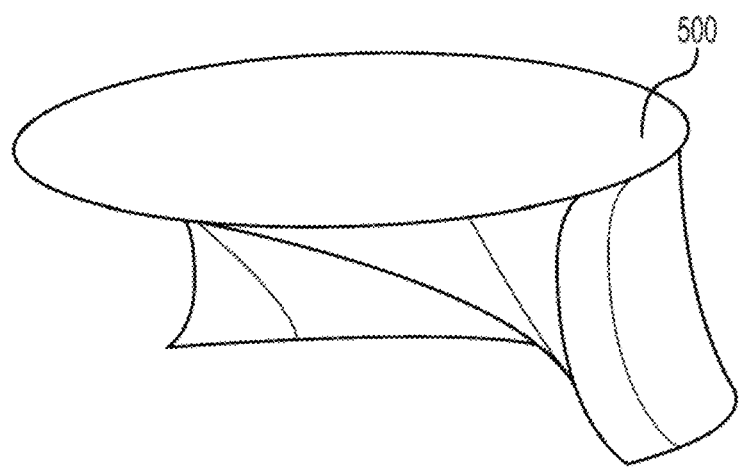
FIG. 18 is a top perspective view of the airflow deflector shown in FIG. 16A suitable for use in practicing exemplary embodiments of this disclosure.

Turning now to FIGS. 16A-18, the airflow pathogen reduction system 100 in some embodiments includes an air deflector 500 and at least one device 200 positioned to discharge treated air towards the air deflector. In one embodiment, the device 200 is mounted on a wall, drawing air in from the region where pathogen concentration is typically the highest through air intake 234 and discharging treated air towards the air deflector 500 as shown in FIG. 16A. In another embodiment, the airflow pathogen reduction system 100 includes an air deflector 600 having at least two devices 200 drawing air in from the floor through air intake 234 and discharging treated air towards the air deflector 600 directly over the center of a room 201 as shown in FIG. 16B. Each air deflector 500, 600 has a surface corresponding with at least one device 200, the air deflector 500, 600 configured to receive treated air and redirect the air flow, FR, to a predetermined position. The predetermined position in one exemplary embodiment is the expected position of an individual. That is, in one embodiment, the air deflector 500, 600 provides that the near horizontal "beam" of cleanest air would be directed into the air provided to individuals in a generally downward and opposing direction. Thus, if one individual were infected, their discharge viral laden air would generally be away from those nearby and downward to the floor for intake to the system 100. A flow of air that separates potentially infected individuals is generally discharged $F_D$ given the assumption that they are facing each other during their congregation orientation. In addition, the air that has just been presented to the individual is directed back into the system 100 for treating before it can infect other individuals. The treated air, $F_T$, in one embodiment, can be discharged high in the room 0.01 towards the ceiling such that the general flow will be downward where an individual's intake air is drawn. Although the air deflector 500, 600 is shown in FIGS. 16A and 16B as an air deflector mounted to a ceiling, it should be appreciated that the air deflector can be disposed in other positions, including but not limited to, a free standing air deflector, a wall-mounted air deflector, and the like, provided that the air deflector 500, 600 is spaced and positioned from the device 200 such that treated air from the device 200 interacts with the air deflector 500, 600 to direct the treated air towards the desired location.

The air deflector 500, 600 is sometimes referred to as an air mirror for directing air towards a target. In one exemplary embodiment, the air deflector 500, 600 is mounted to the ceiling of a room 201, but the air deflector 500, 600 can be a stand-alone deflector or mounted on the wall. The air deflector 500 has a single treated air receiving surface 502 for directing air towards a target as show in FIGS. 17-18. In another exemplary embodiment, the air deflector has multiple surfaces, each surface configured to direct treated air towards at least one target. For example, as shown in FIG. 16B, the air deflector 600 includes two surfaces to direct treated air towards at least two targets. The air directing surface may be concave, or other shape capable of forcing air in a desired direction, including, but not limited to, wedged, frustoconical, pyramidal, elliptical, and linear. The shape configuration, in one embodiment may be dependent on the aspect ratio of the room 201, ceiling heights, number of devices within an area, and number of targets. In one exemplary embodiment, the air deflector 500, 600 is spaced from an airstream outlet and configured to alternate the flow of treated air from the airstream outlet. The flow of treated air may be altered in the horizontal direction and the vertical downward direction to direct a portion of treated air towards a predetermined direction, for example, where an individual is potentially positioned.

It should be appreciated that the position of the air intake, treated air discharge, and air deflector (if used) of the system 100 is adjustable based on the space containing the volume of air to be treated. For example, in a nursing home room, the bed and chair are typically in fixed locations. Thus, the air discharge configuration and device placement can be optimized to ensure the cleanest air is directed to where the individual is most likely to be. More specifically, the apparatus in one exemplary embodiment includes a plurality of outlet ports adjustable to direct a flow of a volume of treated air towards at least one desired location. In an alternative exemplary embodiment, the apparatus includes a plurality of outlet ports disposed at a predetermined position, that is a position known to potentially have individuals requiring treated air, to direct a flow of treated air towards the desired location. The desired location may be a bed or a chair in a nursing home, or chairs around a table in a restaurant or meeting room.

Figure 23:
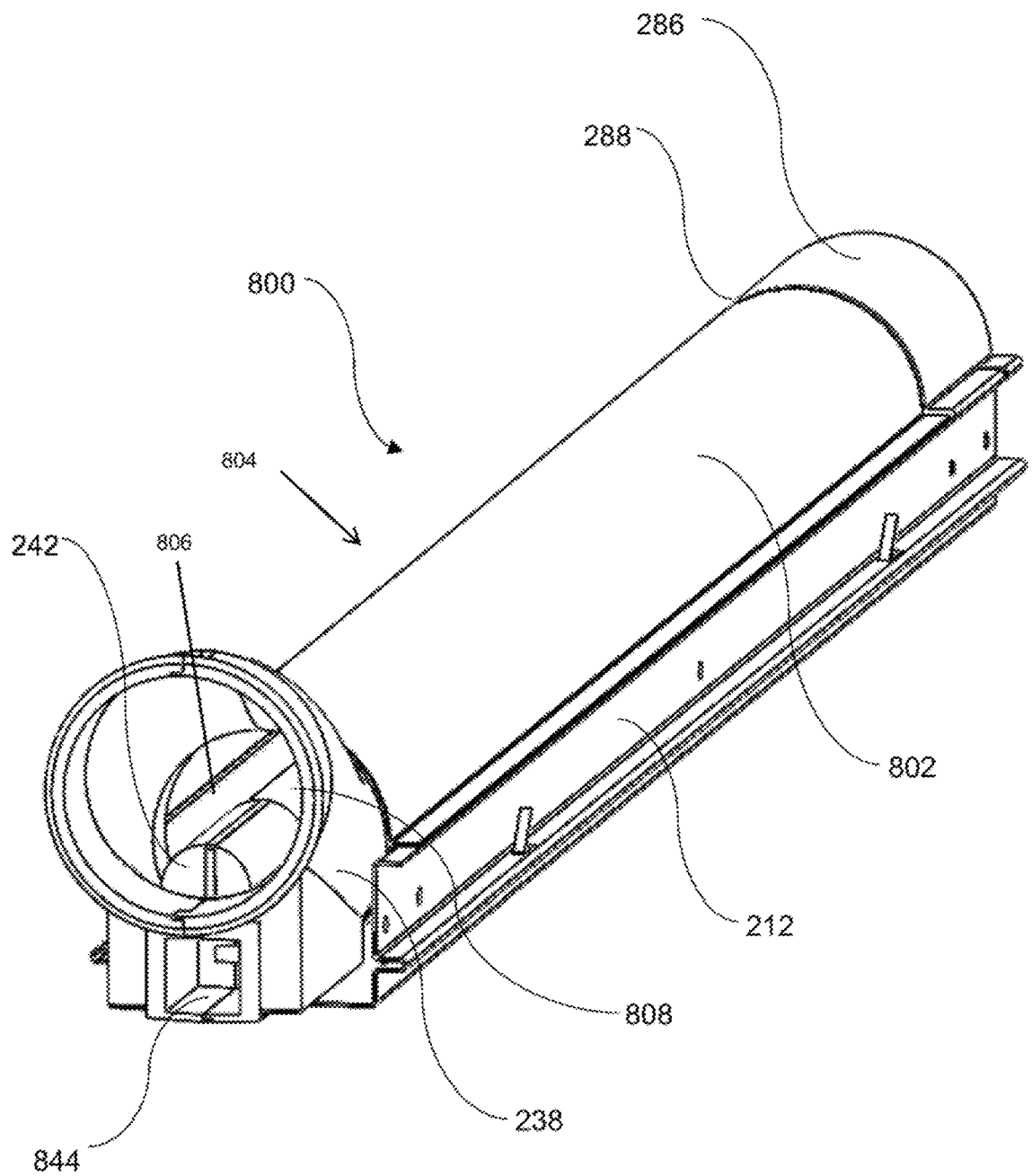
FIG. 23 is a perspective view of an airflow pathogen reduction device suitable for use in practicing exemplary embodiments of this disclosure.
Figure 24:
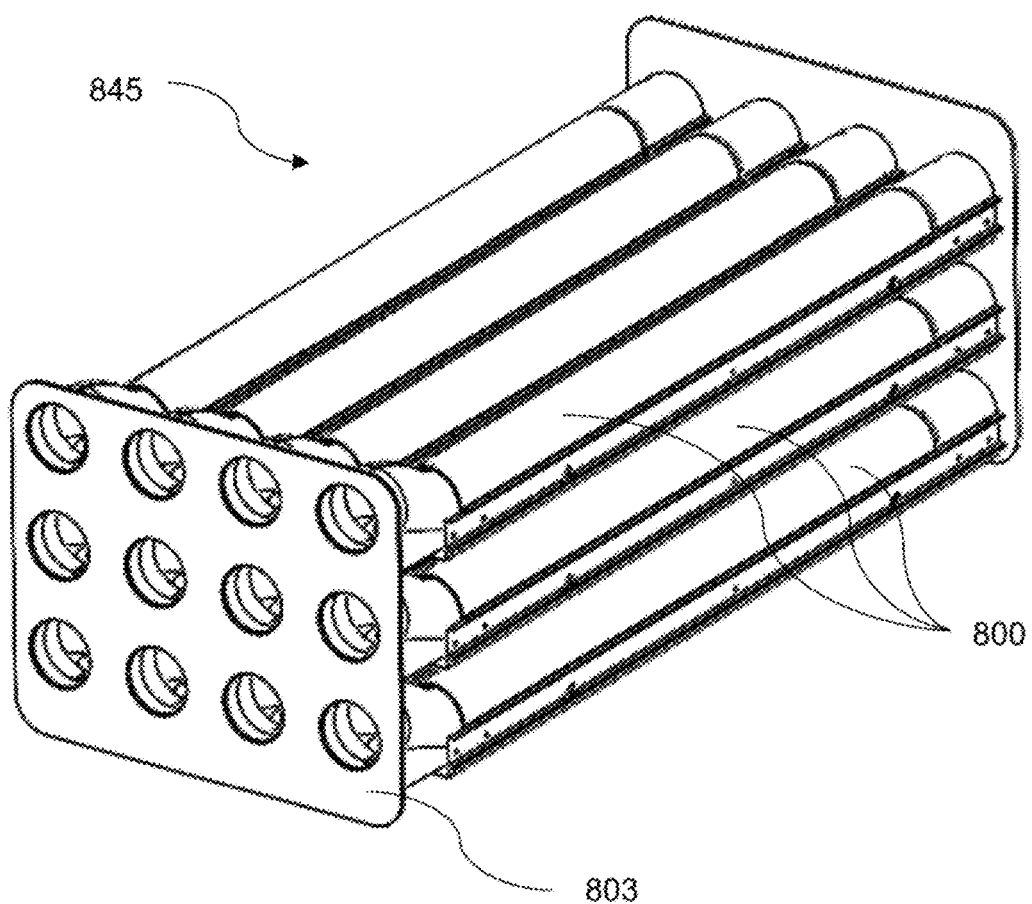
FIG. 24 is a perspective view of the airflow pathogen reduction device showing an array of subassemblies suitable for use in practicing exemplary embodiments of this disclosure.
Figure 25:
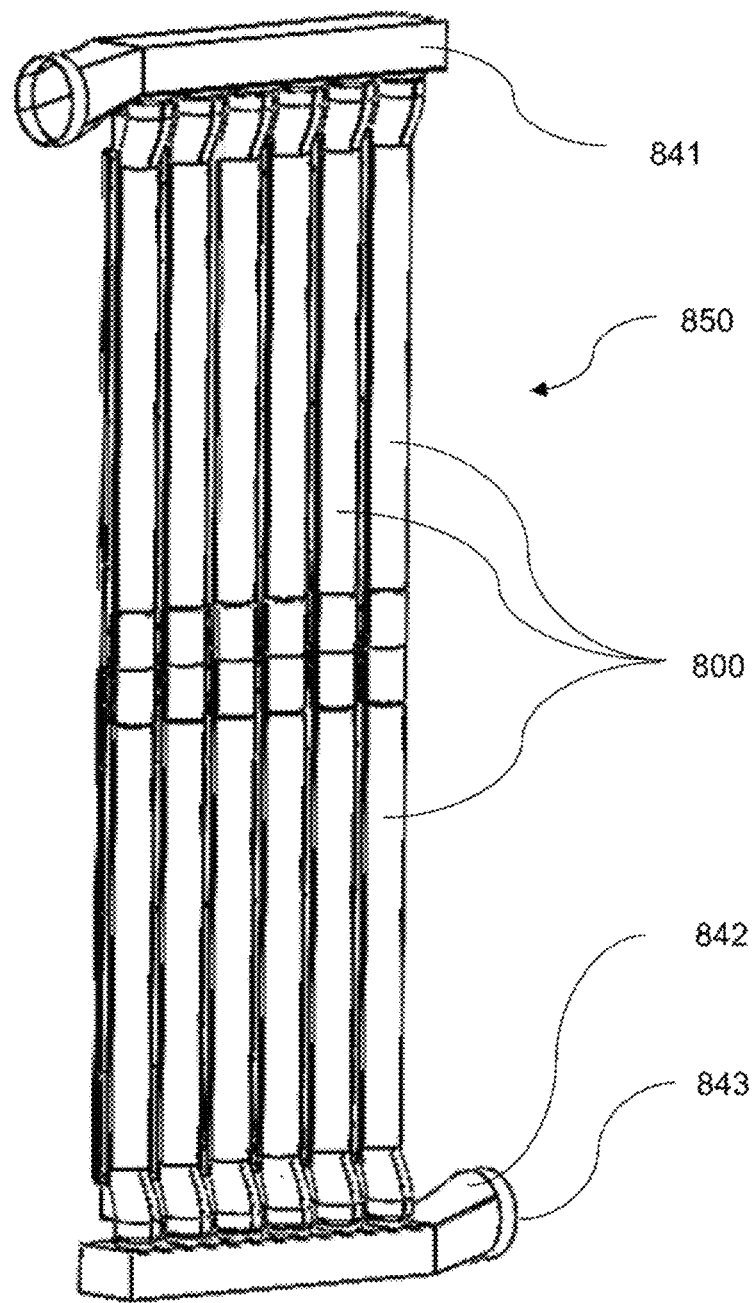
FIG. 25 is a perspective view of the airflow pathogen reduction device showing a set of inline subassemblies suitable for use in practicing exemplary embodiments of this disclosure.

In yet another embodiment, the airflow pathogen reduction device includes either an array of subassemblies or inline subassemblies as shown in FIGS. 23, 24 and 25. Further, in some exemplary embodiments, the design is scaled and integrated into the ductwork of air handling systems in either inline 850 or array 845 methods.

As shown in FIG. 23, subassembly 800 in one exemplary embodiment includes an illumination chamber 802 within an elongated housing 804. The illumination chamber 802 includes a highly reflective layer 806 and a UV-C radiation source 808. In an exemplary embodiment, the layer 806 is a lining or coating having a reflectance as described above. Multi-layers of coatings or linings may further be provided. The illumination chamber 802 further includes UV-C radiation source 808 as a UV generator or UV emitter. The UV-C source 808, in one exemplary embodiment is at least one LED. In another exemplary embodiment, the UV-C source 808 is an elongated bulb or lamp arranged parallel to the flow direction of the air. For example, the UV-C, in an alternative embodiment is a standard low-pressure mercury vapor lamp. The UV-C source 808 may alternatively include an excimer lamp or a pulse xenon lamp as described above. The wall temperature of an illumination chamber 802 having a low-pressure mercury vapor lamp should be approximately 40° C. The wall temperature may be higher than standard mercury vapor lamps due to element doping in the fused silica tubing surrounding the low-pressure mercury vapor lamp that is designed to not pass the 185 nm line generated by mercury vapor. The 185 nm light will produce ozone and therefore must be blocked by absorption in the lamp tubing by the doped material. Such absorption can create additional heat. In an exemplary embodiment, a fan or airflow promoter is part of a separate system. For example, an array 850 of subassemblies 800 as shown in FIG. 24 can be included within a duct system of an HVAC system. In another exemplary embodiment, subassemblies 800 are inline, along a common axis. For example, in the wall mount HVAC type system embodiment, two or more subassemblies 800 can be included with pressurized air provided by the HVAC system. As shown in FIG. 25, the polarity of subassemblies 800 connect to an intake manifold 842 and output manifold 841. Manifolds 841,842 connect to the HVAC rectangular or round ducts 843.

In a duct array where pressure is provided by the HVAC system the array size is based on utilizing the throughput of subassembly 800 at the certified rate. For example, if the throughput of the HVAC system was 250 cfm and the device certification is 125 cfm then 2 subassemblies are required. If the HVAC system was 1250 cfm then 10 subassemblies are needed and so forth.

Elongated housing 804 may further include various sensors and electrical connections to the UV-source 808 and sensors 844 as described above. The subassembly 800 or plurality of subassemblies 800 may further include a user interface 255, input and display as further described above.

Figure 26:
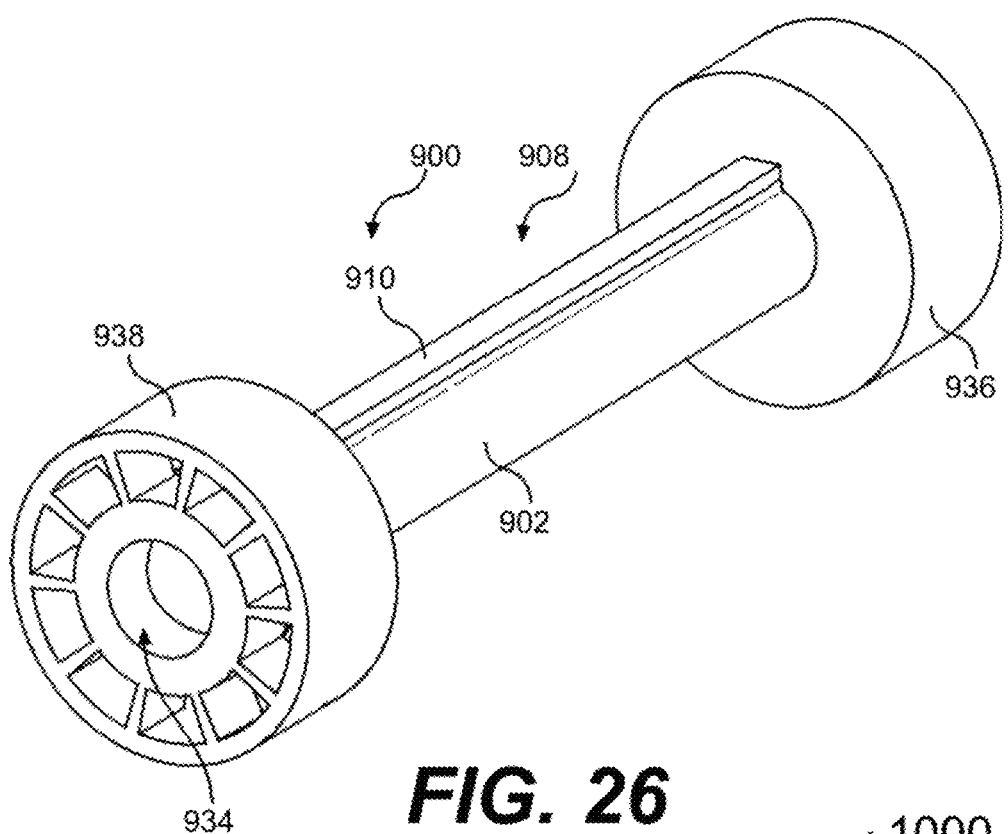
FIG. 26 is a perspective of an airflow pathogen reduction device subassembly suitable for use in practicing exemplary embodiments of this disclosure.
Figure 28:
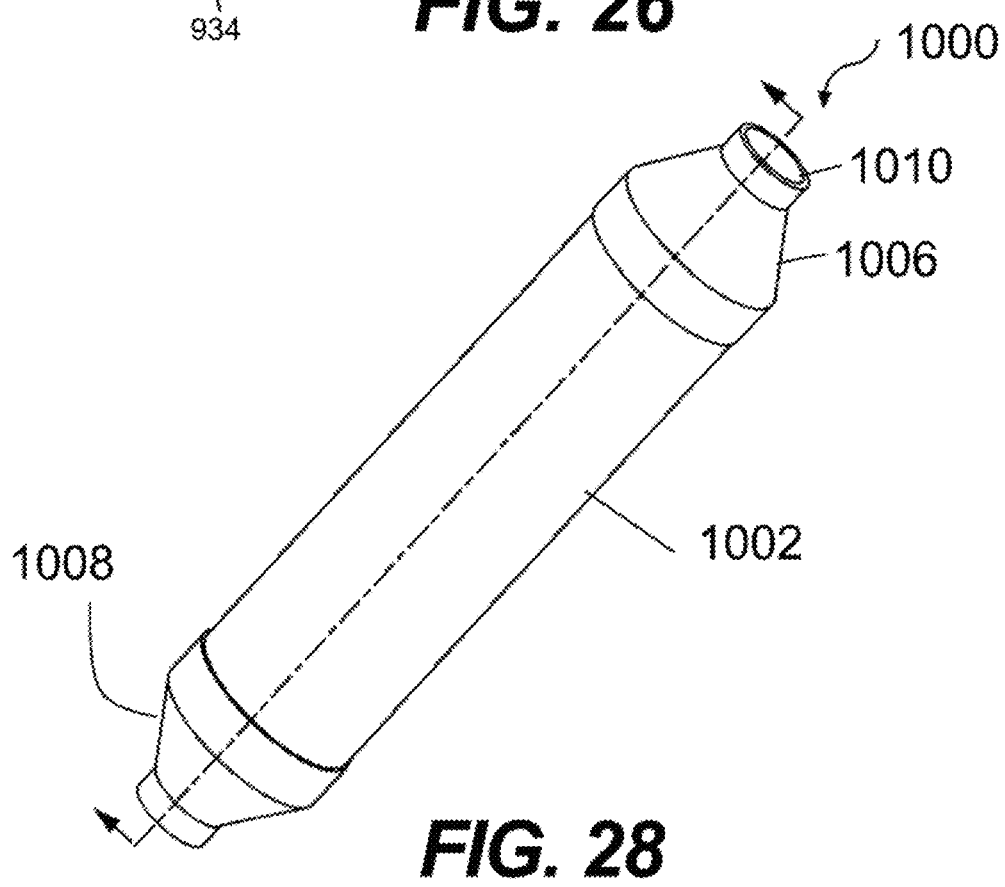
FIG. 28 is a perspective of an airflow pathogen reduction device subassembly suitable for use in practicing exemplary embodiments of this disclosure.
Figure 27:
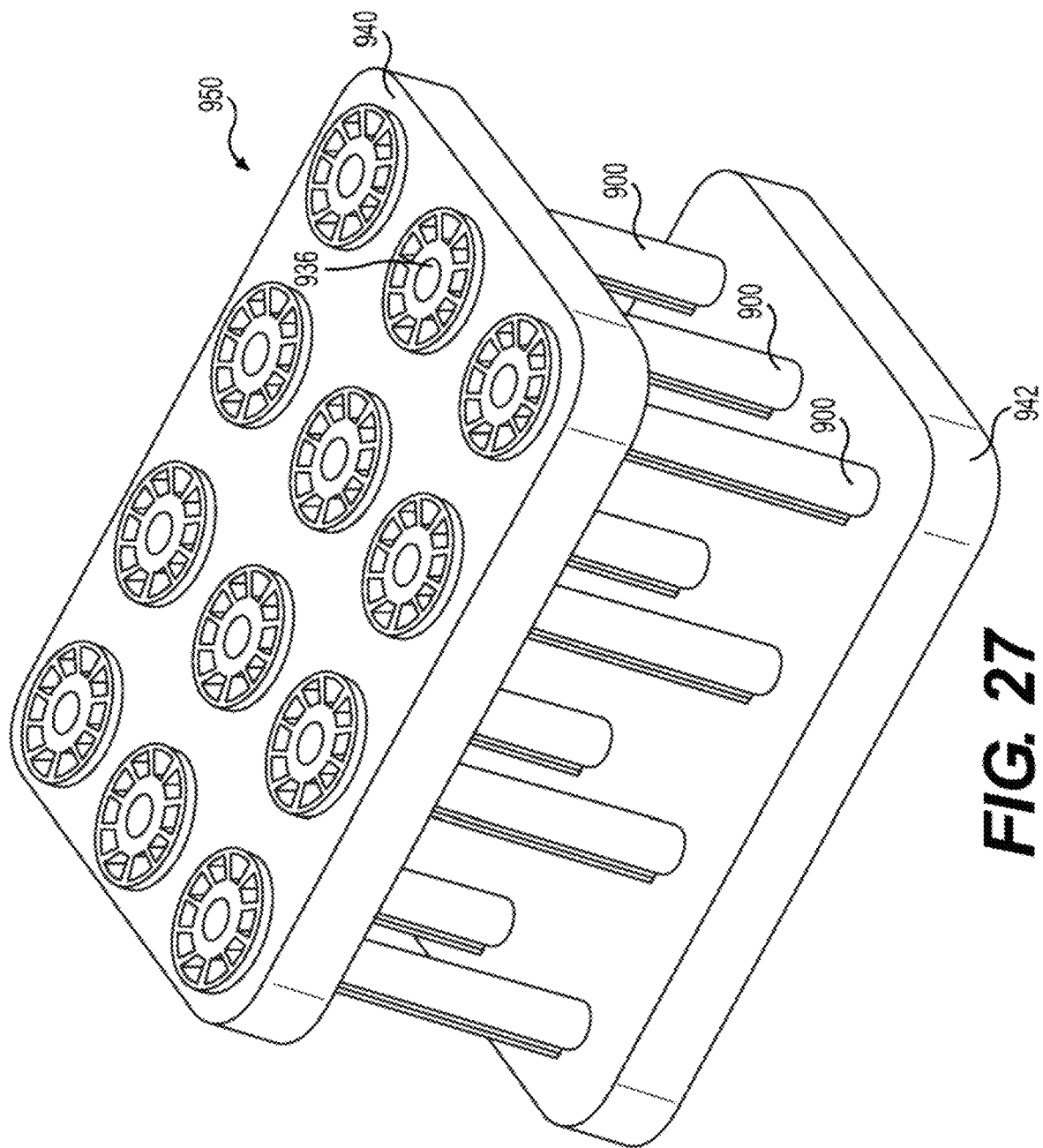
FIG. 27 is a perspective view of an array of airflow pathogen reduction device subassemblies shown in FIG. 26.
Figure 29:
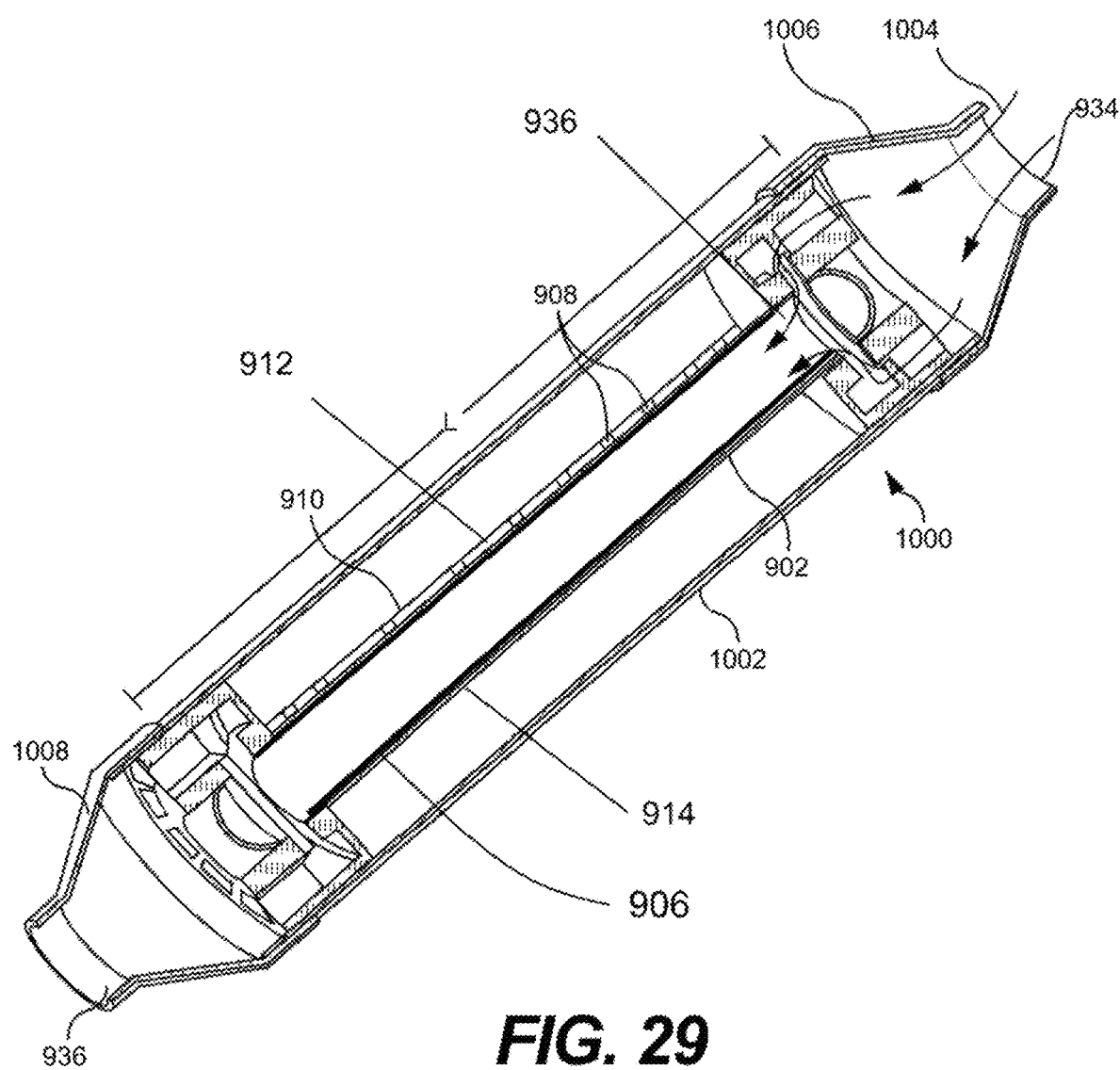
FIG. 29 is a cross-sectional view of the airflow pathogen reduction device subassembly shown in FIG. 28 taken along lines 28-28.
Figure 30:
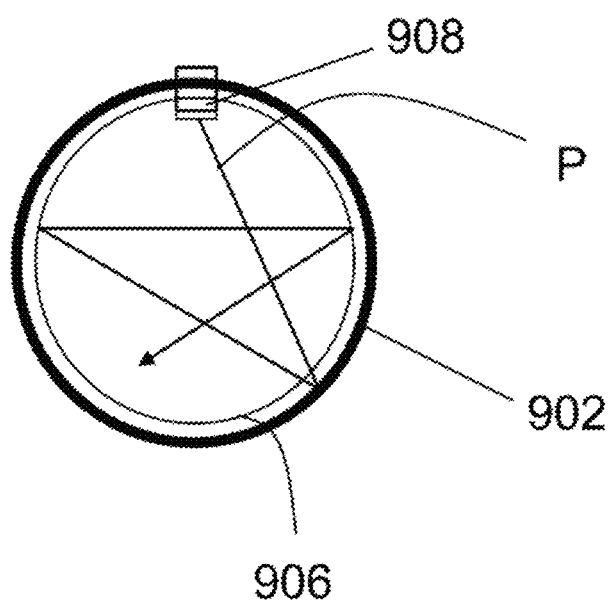
FIG. 30 is a schematic view of an illumination chamber with a UV-source and reflective wall of the airflow pathogen reduction device of FIG. 28 suitable for use in practicing exemplary embodiments of this disclosure.

In another exemplary embodiment, as shown in FIG. 26, the subassembly 900 includes a linear array of UV-C LEDs 910 as the UV-C source 908. The UV-C LEDs 910 can be situated along the length of the illumination chamber 902 behind a fused silica window separating an electronics module and the illumination chamber 902. The subassembly 900 further includes an air intake 934 for intaking untreated air and an air outlet 936 for releasing air treated by the subassembly 900. In an exemplary embodiment, a fan or airflow promoter is part of a separate system. For example, an array 950 of subassemblies 900 as shown in FIG. 27 can be included within a duct system of an HVAC system. In one configuration, a 4×3 array of subassemblies is formed. In one configuration, each subassembly 900 is fixed within a top and bottom plate 940, 942. FIGS. 28-30 show an inline assembly 1000. Inline assembly 1000 includes an outer sleeve 1002, a top cap 1006, and a bottom cap 1008. The top cap 1006 in one embodiment is tapered, conical, or semi-conical in shape to provide a duct reduction into an illumination chamber 802 having a smaller diameter than the outer sleeve 1002. The illumination chamber 902 includes a an inner wall 914 of high UV-C reflectance material 906 and a UV-C source 908. In an embodiment, the UV-C source 908 is UV-C LEDs in a linear array 910 situated along the length of the illumination chamber 902. In an embodiment, the LEDs and an electronics module are behind an optical window 912. The optical window 912, in one embodiment, is a fused silica window. The UV-C source delivers UV-C light through the window 912 into the illumination chamber 902. One possible path that photons emitted from UV light source 902 can take is shown as path P in FIG. 30. The UV-C reflective qualities of the high UV-C reflectance material 906 along the internal wall provide that the UV-C light produced by the UV-C source 908 will emit photons through the window 912, which will travel along a path until the photons reach the internal wall 914 reflect off the high UV-C reflectance material along internal wall 914, and travel in another direction, repeating the sequence of travel and reflect. In one embodiment, the curvature of internal wall 914 is configured to impart multiple reflections within the illumination chamber 902 of any light introduced into the chamber. As provided above, the illumination on the inside surface of illumination chamber 902 is highly reflective, uniform and Lambertian. The UV-C reflectance material 806 coating or lining the illumination chamber 902 is specular and/or diffuse, and a>85% UV-C mirror which will cause the LED produced energy to pass through the illumination chamber 802 multiple times with a randomness creating a near uniform photon density within the illumination chamber 902. In an exemplary embodiment, the layer 906 is a lining or coating having a reflectance in the range of 85%-97%, and more preferable, approximately 90%-97% and even more preferably approximately 97%. In one embodiment, the illumination chamber 902 is formed of an aluminum extrusion and can be fixedly secured to end caps 934, 936.

Within each end cap 934, 936 is a reflector for blocking light, which can reduce or eliminate UV-C light from escaping the illumination chamber 902 and exiting into an occupied space or volume of air. It should be appreciated that the length of the subassembly 1000 can be determined by the required exposure (E=Photon density*time), where t is determined by flow rate and length. Further, it should be appreciated that the Photon density is proportional to the number of LEDs used in the system. The inline subassembly 1000, in an embodiment, has an extrusion length of the illumination chamber 902 of approximately 50 cm and a cross-sectional area of 19.6 cm$^2$. Such an inline assembly 1000 has, in one embodiment, approximately 8 LEDs, such that 10 subassemblies 1000 include 80 LEDS which can deliver approximately 170 m$^3$/hr (1000 ft$^3$/min) of treated air. An array of subassemblies 1000 can be included within a duct system of an HVAC system. In another exemplary embodiment, subassemblies 1000 are inline, along a common axis. For example, in the wall mount HVAC type system embodiment, two or more subassemblies 1000 can be included with pressurized air provided by the HVAC system. In a duct array where pressure is provided by the HVAC system the array size is based on utilizing the throughput of subassembly 1000 at the certified rate. For example, if the throughput of the HVAC system was 250 cfm and the device certification is 125 cfm then 2 subassemblies are required. If the HVAC system was 1250 cfm then 10 subassemblies are needed and so forth. In another embodiment, the extrusion length of the illumination chamber 902 is approximately 600 mm, the diameter of the illumination chamber 902 is approximately 116 mm and the diameter of an opening 1010 of the top cap 1006 is approximately 50 mm. With a throughput of the HVAC system of 100 cfm, the device 1000 can deliver approximately 170 m$^3$/hr (1000 ft$^3$/min) of treated air with 400 Watts.

Figure 31:
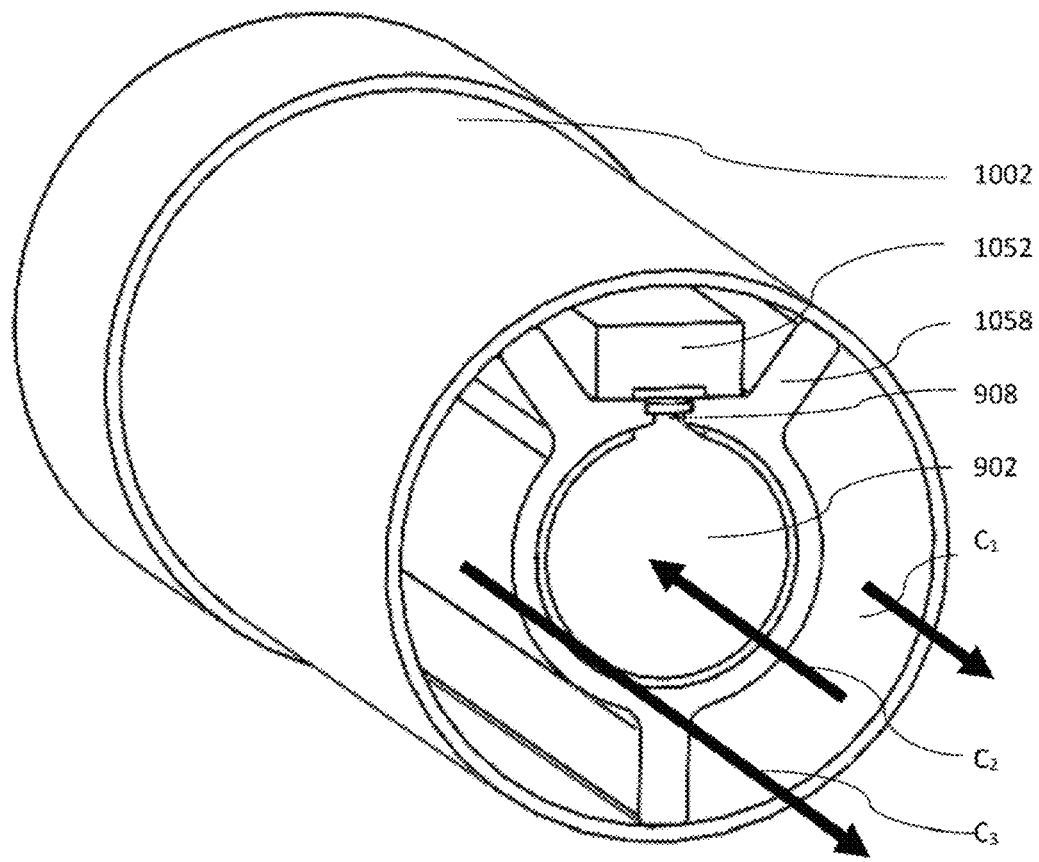
FIG. 31 is a partial perspective view of a body of a subassembly having a heat sink, shown without a top cap.
Figure 32:
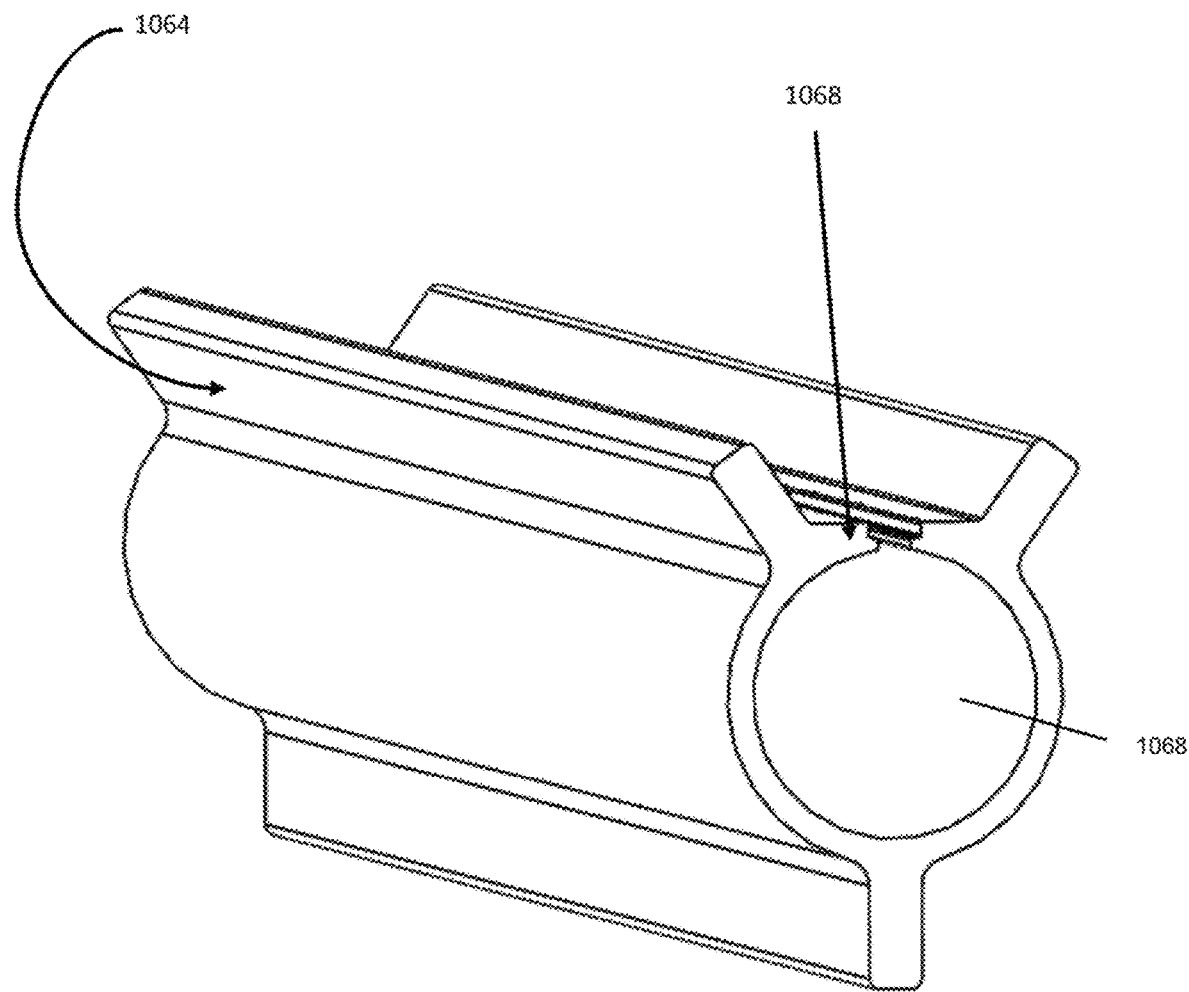
FIG. 32 is a perspective view of an extrusion providing a heat sink of the subassembly shown in FIG. 31.
Figure 33:
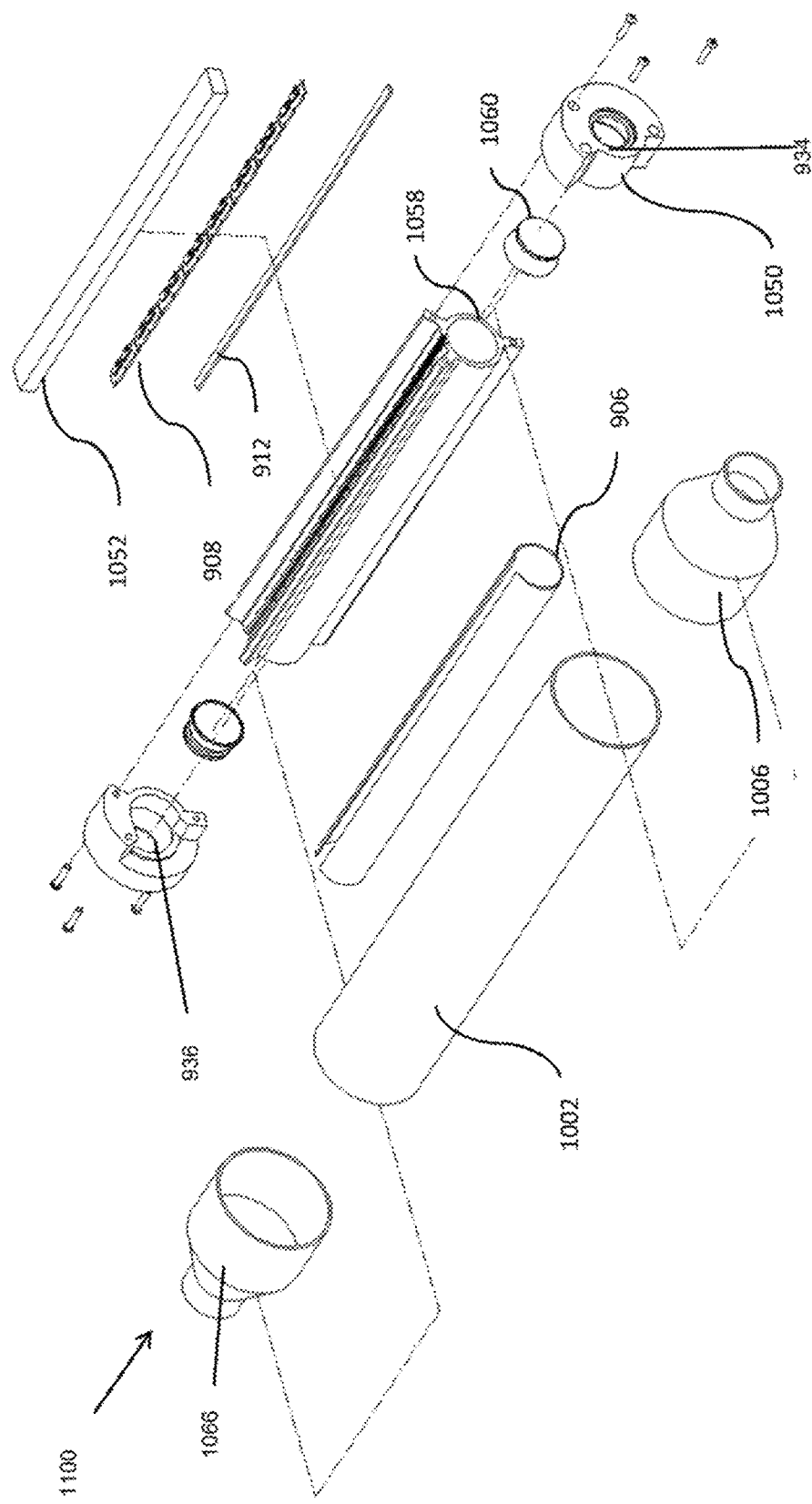
FIG. 33 is an exploded view of the airflow pathogen reduction device subassembly suitable for use in practicing exemplary embodiments of this disclosure.

Turning now to FIGS. 31-33, in another embodiment, a subassembly 1100 includes a linear array of UV-C LEDs as the UV-C source 908. The UV-C LEDs can be situated along the length of the illumination chamber 902 behind a fused silica window 912 separating an electronics module 1052 and the illumination chamber 902. The subassembly 1100 further includes an air intake 934 for intaking untreated air and an air outlet 936 for releasing air treated by the subassembly 900. In an exemplary embodiment, a fan or airflow promoter is part of a separate system. For example, an array of subassemblies can be included within a duct system of an HVAC system. Subassembly 1100 further includes an outer sleeve 1002, a top cap 1050, and a bottom cap 1006. The top cap 1050 in one embodiment is tapered, conical, or semiconical in shape to provide a duct reduction into an illumination chamber 902, which has a smaller diameter than the outer sleeve 1002. The illumination chamber 902 includes an inner wall 1068 of high UV-C reflectance material 906 and a UV-C source 908. In an embodiment, the UV-C source 908 is UV-C LEDs in a linear array situated along the length of the illumination chamber 902. In an embodiment, the LEDs and an electronics module 1052 are behind an optical window 912. The optical window 912, in one embodiment, is a fused silica window. The UV-C source delivers UV-C light through the window 912 into the illumination chamber 902. The illumination chamber 902 in this embodiment is formed by an extrusion 1058 having extensions 1064 extending radially therefrom. The extensions 1064 and outer sleeve 1002 form channels for air to flow. Thus, the extensions 1064 in one embodiment are heat sinks to help maintain a desired temperature within the subassembly 1100. One possible path that airflow can take is shown in FIG. 31, wherein air flows along air channel $C_1$ along and a first heat sink to channel $C_2$, which is the illumination chamber 902 where the air is treated by UV-C source 908 to reduce the concentration of pathogens in the airstream, and finally through channel $C_3$ where the treated air exits the subassembly 1100. The cross sectional area of each of these channels is approximately equal to the incoming duct cross section providing a near constant air flow velocity through the system and minimizing air resistance. Air flowing along the extensions 1064 of the extrusion 1058 removes heat on each side via convection from the air passing by. It should be appreciated that the highly reflective liner or coating 906 is an insulator so not much heat via convection happens from the air passing through the illumination channel 902. As shown in FIG. 31, heat enters the extrusion 1058 by conduction from the LEDs to a copper thermal management circuit board 1068 and then into the extrusion 1058 by conduction. The subassembly 1100 is designed for a constant cross section in the air flow, which is equal to the cross section in the incoming duct of the HVAC system. Thus, the cross-section of outer sleeve 1002 in one embodiment is three times the duct cross section plus the electronics cavity (908,1052, 912) and the volume of the extrusion 1058 with extensions 1064.

Highly UV-C reflective illumination chamber end caps 1060 direct photons escaping the chamber back in thereby increasing the photon density within the chamber. A gap between chamber extrusion 1058 and cap 1060 enables air to pass into and out of the illumination chamber. In subassembly 1000 the air path is shown 1004 and makes a "single pass" through the system. Subassembly 1100 utilizes a "triple pass" such that an increased amount of heat can be removed enabling a higher photon density without system overheating. Given the current state of inefficient electrical to optical power conversion UV-C LEDs subassemblies such as 1100 are preferred to obtain adequate exposure. The triple pass creates a higher flow resistance and therefore requires a higher pressure for a given system cfm than subassembly 1000.

The primary development goal of UV-C LED technology is to improve the electrical to optical energy conversion efficiency. It is predicted that the current state of the art of 6% efficiency may be increased to 50% by 2030. Subassemblies 1000 reduced flow restrictive load on the HVAC system as efficiencies improve.

Thus, it should be appreciated that the device 200, 300, 400, 450, 800, 900, 950, 1000, and 1100 includes various positions for the airstream inlet for untreated air and the airstream outlet for treated air. The airstream inlet for untreated air, in one exemplary embodiment, is generally positioned along the perimeter of an area. In another exemplary embodiment, the air intake is spaced from the perimeter of an area, or more centrally located in a room 201 or area. Similarly, the airstream outlet may be positioned along the perimeter of an area or more centrally located in the room 201 or area. The apparatus air intake(s) and outlet(s) can be configured according to a predetermined location of individuals and can be adjustable. The airstream outlet for treated air in some exemplary embodiments, is between at least 2 feet and 10 feet above the airstream inlet.

User Interface

Figure 19:
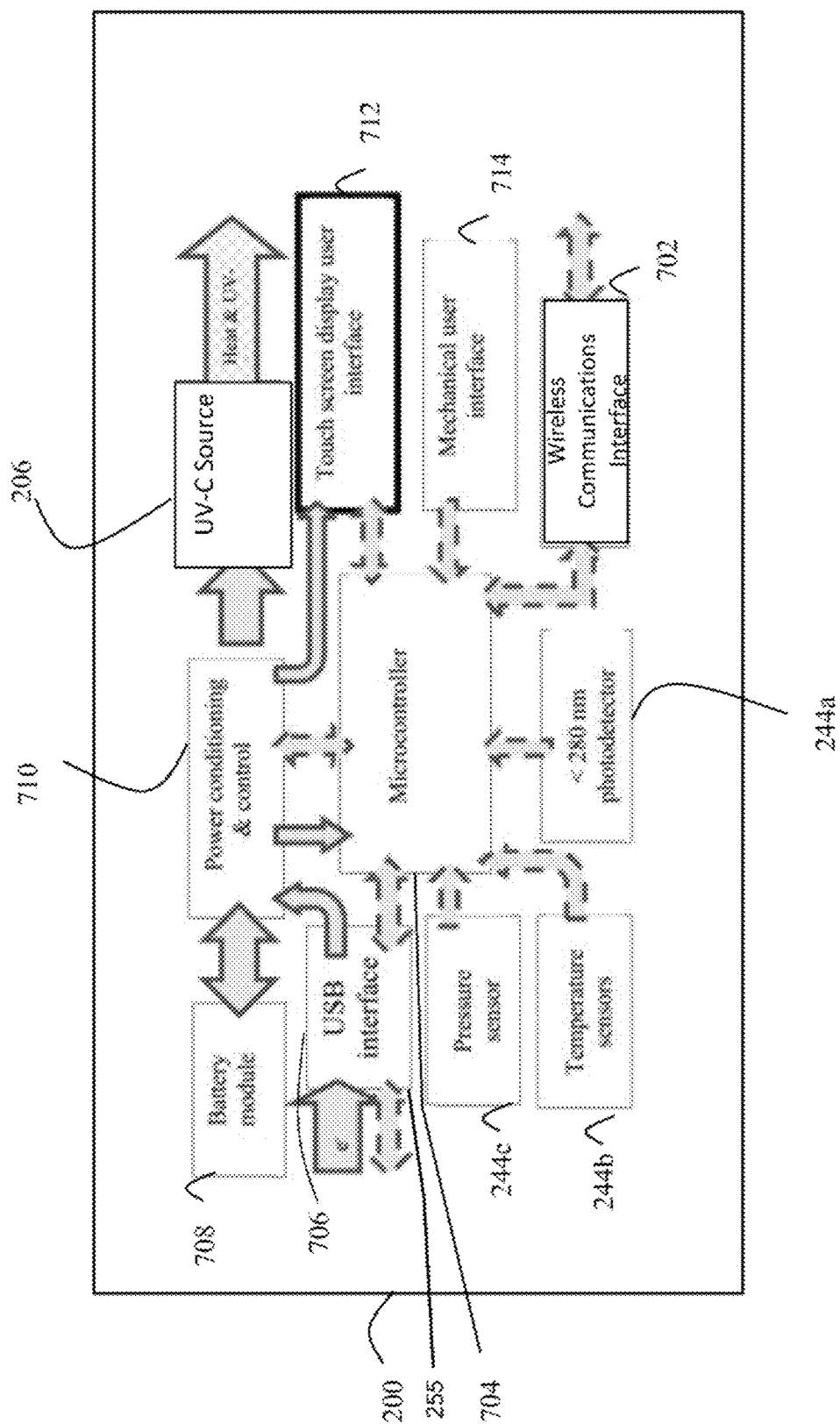
FIG. 19 is a schematic view of the airflow pathogen reduction device suitable for use in practicing exemplary embodiments of this disclosure.
Figure 20:
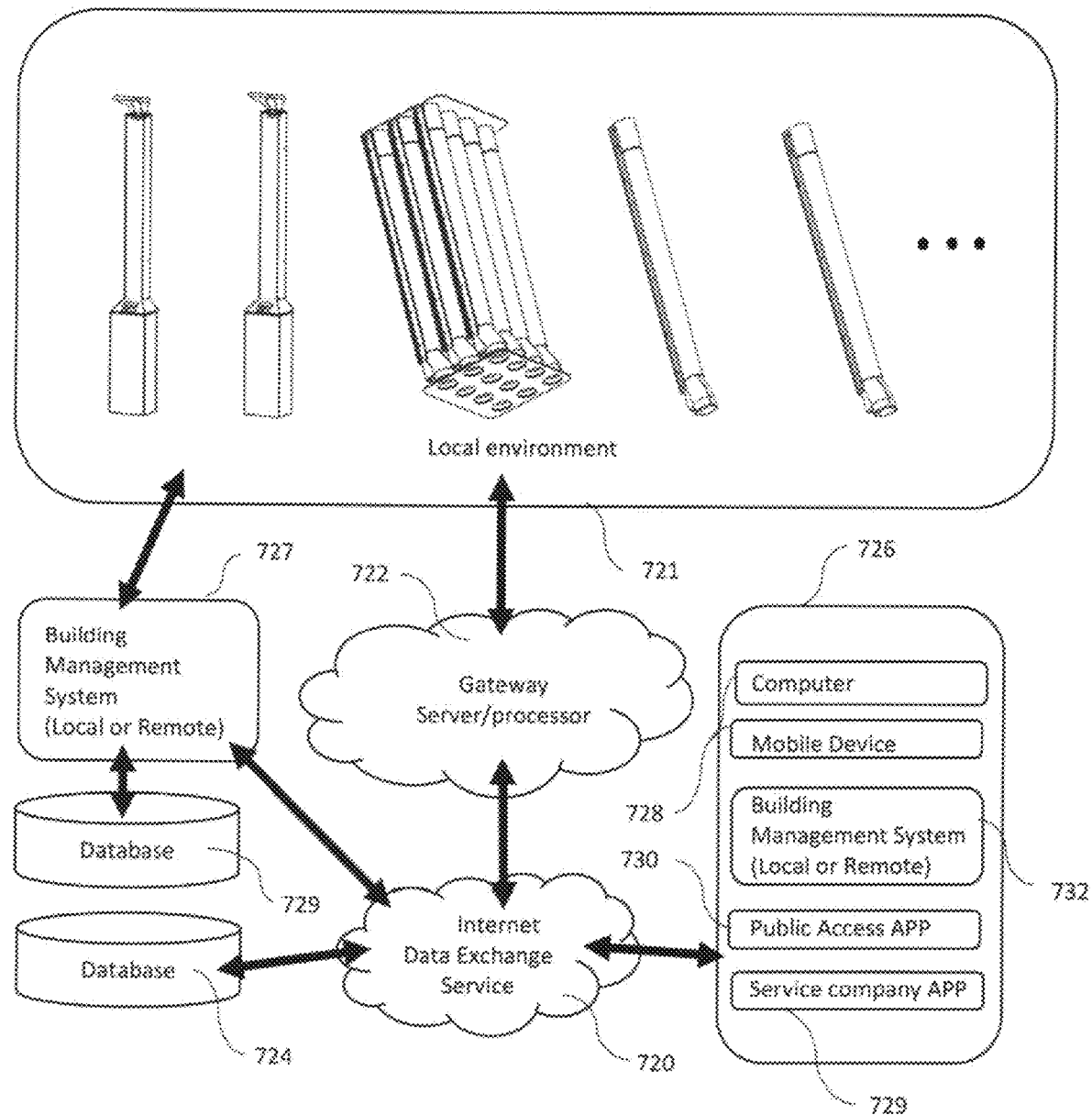
FIG. 20 is a schematic view showing a network of airflow pathogen reduction devices suitable for use in practicing exemplary embodiments of this disclosure.
Figure 21:
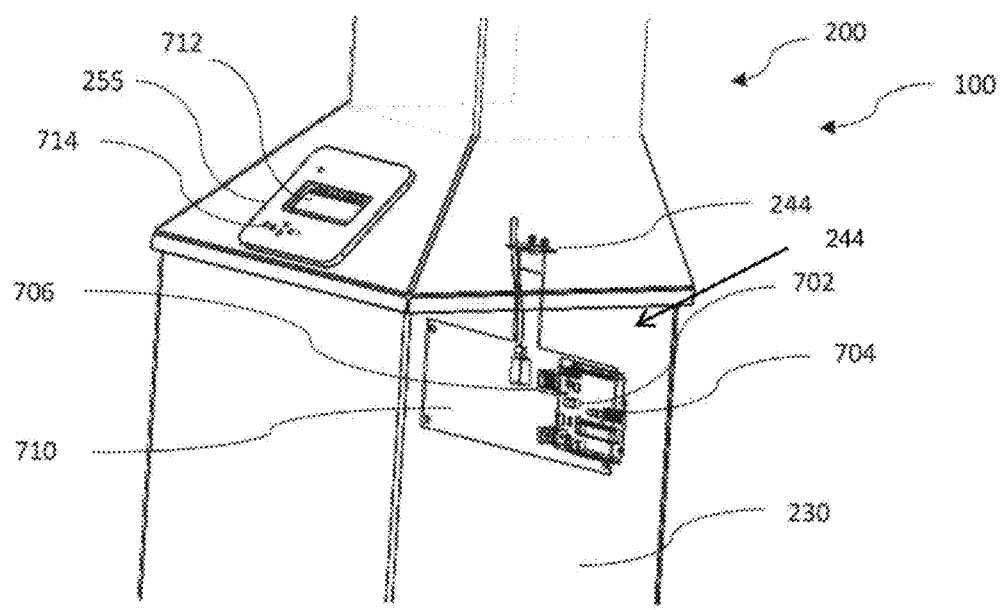
FIG. 21 is a partial perspective view of the airflow pathogen reduction system shown in FIG. 1A showing the user interface suitable for use in practicing exemplary embodiments of this disclosure.

Turning now to FIGS. 19-21, the device 200 may include a communication module for wirelessly communicating with a network for receiving communications with a system 100. As shown in FIG. 19, a wireless communication interface 702, including, but not limited to a blue tooth interface, communicates with a controller (or microcontroller) 704, which enables information exchange between the device 100 and an end user's device, including but not limited to, a phone, tablet or personal computer. Android, iOS, Windows, or other operating systems can be linked to the system 100 to provide notification alerts to the user along with system status information. In reverse, information from the sensors 244 in the phone or web connection may be utilized by the microcontroller within the device along with software or firmware updates. In an embodiment, the controller 704 is configured to operate the device 200 wherein the controller 704 is integrated into a control board of the device 200. The controller includes electrical circuits, such as signal processors, and can be implemented as a programmed chip, as well as a dedicated processor or circuitry. The controller can be readily programmed to perform the recited calculations, or derivations thereof, to provide determinations of the detector as set forth herein. The controller 704, in certain embodiments, may communicate with a router using any suitable wireless communication protocols including, but not limited to, LoRaWAN, Wifi, Bluetooth, M2M, cellular, Narrow Band IoT, and Azure.

In certain embodiments, sensors 244, which can include, for example, a UV-C monitor sensor 244a, a temperature sensor 244b for measuring temperature of the illumination chamber 202, and a pressure sensor 244c for detecting a change in pressure between the illumination chamber 202 and the lower enclosure 230 as a measure of flow, are operatively connected to the microprocessor 704.

Certain embodiments may include additional connection interfaces, for example, a USB interface 706, operable to provide a connection between the device 200 and an end user's device and to transfer digital data. The system 100 is operably connected to a power source, which in one embodiment is a battery module 708. In another embodiment, the device 200 is operably connected to a wired power source. The UV-C source 208 for providing UV-C light in the illumination chamber 202 may be operatively connected to a power conditioning and control 710. The device may further include at least one user interface. In one embodiment, the user interface includes a touch screen display 712 and a mechanical user interface 714, which communicates directly to the controller 704.

In some cases, the controller 704 communicates directly with the sensors 244, the USB interface 706, the power conditioning and control 710 and the user interface(s) 712, 714.

Turning now to FIG. 20, it is contemplated that a plurality of devices 200 can be controlled over a wireless communication interface 702. An M2M interface may be employed for a connection to cloud data exchange services 720. Machine to Machine (M2M) is one method for the Industrial Internet of things (IIoT) and the more consumer-oriented Internet of Things (IoT). In one embodiment, the plurality of devices 200 communicate with a router 722 via a wireless communication protocol and the router 722 communicates with the cloud data exchange service 720. In an embodiment, the cloud data exchange service 720 is a cloud-based server or processer coupled to a database 724. In the remote environment 726, an end user's device or devices 728, whether or not mobile, including but not limited to, a phone, tablet or personal computer, can communicate with the cloud-based data exchange service 720 and/or processor though the internet. In certain exemplary embodiments, each device 200 can be controlled through the use of user devices 728. In other embodiments, certain user devices 728 receive information from the device(s) 200 through the internet/ cloud 720, without the ability communicate directly with the device(s). For example, device 200 or plurality of devices 200 may provide information that includes, but is not limited to, air treatment device maintenance data, operational status data, lamp use data, and location data. In yet another embodiment, some devices 200 in the remote environment 720 have the ability to control the devices 200 in the local environment 721 while other devices in the remote environment are unable to control the air treatment devices in the local environment. While in some exemplary embodiments, the wireless router, M2M or Bluetooth permits the devices to communicate to each other as well as to an adjacent wired local area network (LAN), other embodiments may only allow communication among the air treatment devices in the local environment.

Such data can also be available to the public. Utilizing computer applications 730 such as but not limited to Apps for phones, Web interfaces and computer programs, a given portion of the data could be accessed. As an example, the number of running devices at a restaurant could be accessed by a potential diner considering where to eat. The mobile device app would show nearby restaurants with safer air thereby providing additional confidence for eating out. Additional information could also be communicated such as: links to web sites, room temperature, or open table counts from other smart machines at the restaurant.

Since in some embodiments the system becomes part of the overall HVAC system communication between the device and the HVAC system 727 enables the two smart systems to share data 729 and adjust for optimal performance of cleaning air combined with user comfort.

For example, in a "shared" HVAC system, where the return air from three separate tenants gets mixed heated or cooled and sent back to the tenants, it is known that aerosol-based pathogens are small enough to pass through filters and can stay airborne for hours. Thus, pathogen contaminated air is also shared. The pathogen reduction system 100 working together with the HVAC system provide an optimized lower risk situation for individuals and assist in reducing pathogens for all three tenants.

Alternatively, the plurality of devices 200 can be controlled by a controller or smart machine, which collects data from the sensors 244 of the plurality of devices 200, communicates that data with the integrated system, and makes process control adjustments based on that communication. The plurality of devices 200 work together through a host network, for example, a wireless communication network, wherein the controller provides a user interface to the data and devices 200, monitors the system performance, and provides predictive maintenance information 729.

In one embodiment, each device 200 or a plurality of devices 200 in one local environment, for example a home environment or a business or restaurant environment may include a wireless communication device for purposes of connecting to a wi-fi network and server/processor, for example, through a wireless router or other type of wireless hub.

In yet another embodiment, the system is smart machine enabled by IIoT or IoT integration. Each device 200 would communicate through the network which communicates with a server in the cloud 720. Access to that data of the devices 200 can be configured for several purposes. The devices 200 can be configured to notify its owner of an upcoming maintenance such as filter changes or lamp changes or monitor the system parameters and performance derived from the sensors along the air flow path. In one embodiment, a contracted maintenance company can be alerted for maintenance scheduling 729. In certain embodiments, a user's device can communicate with a user's phone for direct access without cloud components.

Exposure

Included in the illumination chamber 202 is a UV-C source 208. Gas moving through a closed system has a well-defined relationship between the velocity of the gas and the cross-sectional area of the flow channel. To determine the magnitude of the radiation dose, the Exposure needs to be calculated as defined by:

Exposure=Photon density*time in units of $$\frac{mW}{cm^3}$$

times time in $s$ provides exposure in $$\frac{mJ}{cm^3}$$

The time a unit of air is radiated (residence or travel time) is dependent on the path length of the illumination chamber 202 (radiation cavity) and speed of the air through the illumination chamber 202.

Velocity=Flow rate/cross-section

Flow rate $Q$=system throughput in $$\frac{m^3}{s}$$

Time=path length/velocity

Reducing the cross-section of the illumination chamber 202 to increase intensity is counter intuitive since Exposure may go down due to a greatly increased speed of the air through the illumination chamber. Increasing the illumination cross section to increase the time duration that pathogens are within the chamber creates a lower photon density along the outer walls of the chamber reducing exposure for pathogens traveling in that region. Further describing pulse modulated light is inappropriate since the air still moves during the "off" time of modulation, thereby allowing pathogens to pass through at least a portion of an illumination chamber with no exposure to the UV-C energy. Exposure in this case would be calculated only during the "on" times. The optimum chamber cross section is a function of the illumination source, chamber length, wall reflectance, desired throughput in cfm and specified pathogen single pass survival. Since Exposure, as measured in joules of UV-C energy per exposure chamber volume is the primary purpose of UV-C based pathogen reduction systems, the present system improves upon existing systems in part by implementing significantly higher Exposures utilizing a linear length of high UV-C reflectance surfaces, such as, but not limited to mirrored anodized aluminum.

In one embodiment, the illumination chamber includes a diameter of 101.6 with a bulb diameter of 25.4 This provides a cross-sectional area of the illumination chamber of 7600.6 mm² and path length of 1219.2 mm. Using a flow rate of 125 cfm, and the cross-sectional area, the velocity in the air channel is 7729.6 mm % s. Thus, the time in the exposure cavity is 15.8 ms. Exposure for a 75 watt bulb is 1.7 millijoules/cm³, wherein the bulb produces 22.5 watts of light and 20.25 watts at 254 nm. Such Exposure calculation utilizes an optical multiplier of 5, as discussed below, resulting from the highly reflective surface of the illumination chamber, which provides a UV-C effective power of 101.3. As such, the survival fraction for one pass with an MS2 pathogen is 0.52 and the calculated exponent k' factor for MS2 is −0.37499. Studies have shown that the MS2 is 10-times more difficult to kill than SARS-CoV-2; thus, the survival rate for SARS-CoV-2 is expected to be lower.

Figure 22:
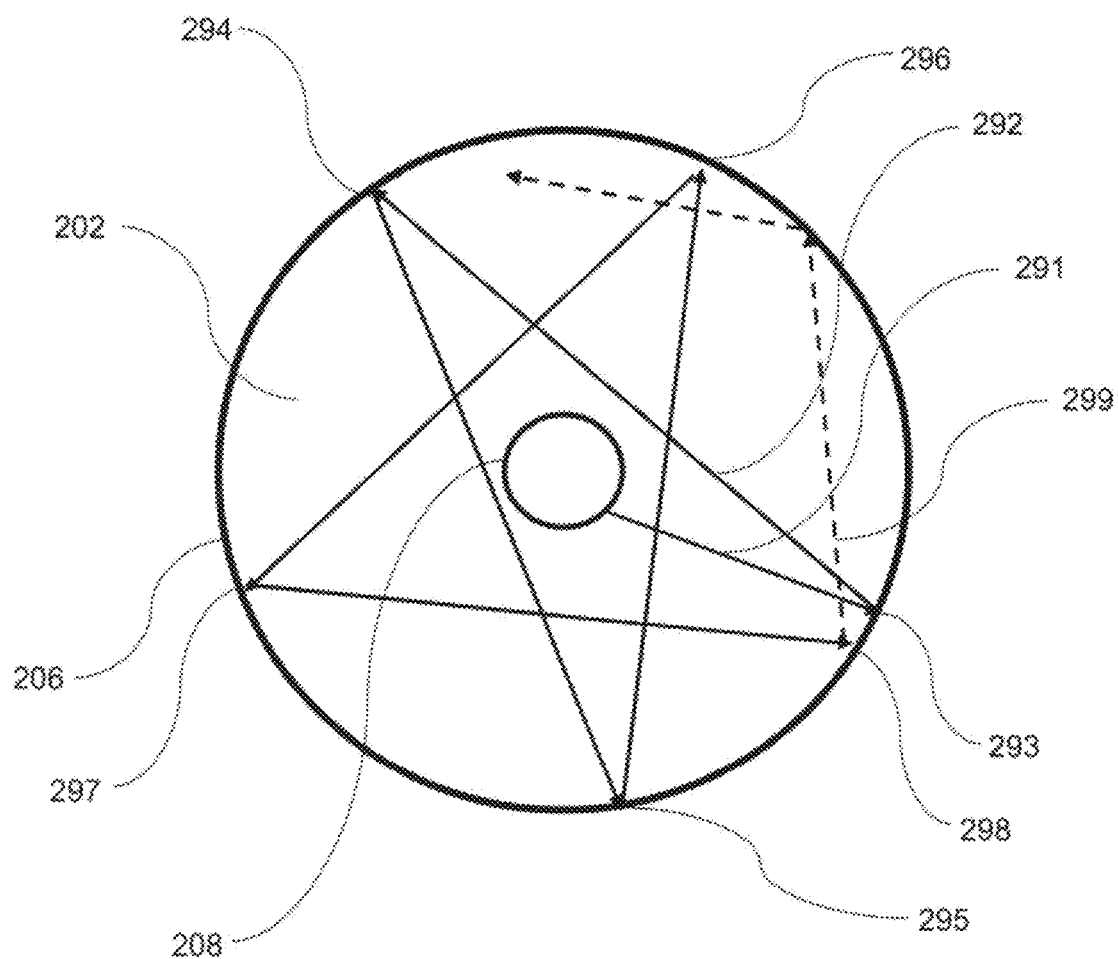
FIG. 22 is a cross section of an illumination chamber with a UV-source and reflective wall of the airflow pathogen reduction device of FIG. 1A suitable for use in practicing exemplary embodiments of this disclosure.

There exists an "re-use" of the source photons such that there is a multiplicative effect of the generated source power. FIG. 22 details the concept showing a cross section of the illumination chamber 202 with source 208 and reflective wall 206. Consider an optical "ray" 291 generated by the source 208 consisting of 100 photons. This ray travels in a straight line and strikes the reflective surface 206 at location 293 with an angle of incidence to the normal of the reflective surface. If the surface has a 90% reflectivity in the UV-C wavelength region 90 photons would be contained in the reflected ray 292 leaving the surface at the same angle of incidence on the other side of the normal. At 294 the ray would be reduced to 81 photons, then at 295 to 73 photons, then at 296 to 65, at 297 to 59, and at 298 to 53. This process would continue until the ray was diminished. Considering only the first 6 reflections the sum total of photons passing through the chamber is 522. This relates to a greater than 5 multiplication of the photon density within the chamber increasing the probability pathogens are struck.

Continuing with this embodiment example, this effectively increases the usable power of the lamp 208 from 20.25 UV-C watts to 101.25 watts of power confined within the chamber from a lamp that consumes 75 watts of electrical power. This relates to a power efficiency of 101.25/75 which equals a system electrical to effective optical power efficiency of 1.35 or 135%

In another embodiment, the illumination chamber includes a diameter of 101.6 with a bulb diameter of 20. This provides a cross-sectional area of the illumination chamber of 7793.2 mm² and path length of 1219.2 mm. Using a flow rate of 125 cfm, and the cross-sectional area, the velocity in the air channel is 7538.7 mm/s. Thus, the time in the exposure cavity is 16.1 ms. Exposure for a 200 watt bulb is 4.6 millijoules/cm³, wherein the bulb produces 60 watts of light and 54 watts at 254 nm as the lamp efficiency is approximately 30% and 90% of the light produced is at 254 nm. At this wavelength the peak sensitivity is down 10%, so there is 48.6 watts of deactivation energy. Using the multiplicative nature of the highly reflective cavity, a gain of at least 5 times is achieved due to "reusing" the generated light by passing back through the air in the chamber. Such Exposure calculation utilizes an optical multiplier of 5 resulting from the highly reflective surface of the illumination chamber, which provides a UV-C effective power of 270. Using the k' of −0.3499, the survival fraction with an MS2 pathogen is 0.17 Again, the survival rate for SARS-CoV-2 is expected to be lower. Further, with 48.6 watts of deactivation energy from a 200 watt energy source, an optical multiplier of 5 provides 243 watts of deactivation energy.

In yet another embodiment, the illumination chamber includes a diameter of 101.6 with a bulb diameter of 20. This provides a cross-sectional area of the illumination chamber of 7793.2 mm² and path length of 1542 mm. Using a flow rate of 250 cfm, and the cross-sectional area, the velocity in the air channel is 15,077.3 mm's. Thus, the time in the exposure cavity is 10.2 ms. Exposure for a 375 watt bulb is 3.7 millijoules/cm$^3$, wherein the bulb produces 97.5 watts of light and 87.75 watts at 254 nm. Such Exposure calculation utilizes an optical multiplier of 5 resulting from the highly reflective surface of the illumination chamber, which provides a UV-C effective power of 438.8. As such, the survival fraction, using the k' of −0.3499, with an MS2 pathogen is 0.25 and is expected to be even lower for SARS-CoV-2.

The device 200 in one embodiment includes an illumination chamber having a cross-sectional area in the range of approximately 7,600 mm and 18,000 mm$^2$ and a chamber path length of approximately 1,200 mm to 1,600 mm and provides an MS2 pathogen survival fraction in the range of 0.17 and 0.52. In an exemplary embodiment, the device 200 includes an illumination chamber having a cross-sectional area in the range of approximately 7,600 mm$^2$ and 7,800 mm$^2$ and has an MS2 pathogen survival fraction of 0.17 and 0.52. In yet another exemplary embodiment, the device 200 includes an illumination chamber having a cross-sectional area in the range of approximately 7,600 mm$^2$ and 18,000 mm$^2$ and has an MS2 pathogen survival fraction of less than 0.05.

In one exemplary embodiment of the present system, a linear array of UV-C LEDs is situated along the length behind a fused silica window separating the Electronics module and optical radiation chamber. The illumination on the inside surface of an Optical Integration sphere is very uniform and Lambertian. While the apparatus of the present system is not spherical and the present surface specular, not diffuse, the interior optical surface of the present illumination chamber is a greater than 85% UV-C mirror and will cause the LED produced energy to pass through the illumination chamber more than once with a randomness somewhat uniform in nature on the interior surface of the illumination chamber. As example, if 100 photons leave the UV-C source, such as an LED, in a direction (Light Ray), 85 will bounce off an anodized aluminum mirror surface of the present illumination chamber and travel back through the intake air. These 85 photons bounce again to 72 then 61, 52, 44, 37, 32, 27. After just 9 reflections the effective number of photon passes is 512. This gain multiplies the photon density calculation by a factor over 5. It is understood that photons absorbed by pathogens (where the photon energy is converted into the destruction of RNA bonds) reduces the number of photons but accomplishes the objective of destruction of the pathogens. As such, an optical multiplier of 5 is used in the Exposure calculations set forth above.

It is contemplated that specialized coatings can improve the reflectance to 97% if desired. These coatings can include a UV-C reflectance sheet from Porex Filtration Group that reflects 97% of UV-C light. Repeating this example with the interior of the illumination chamber either coated or lined with a sleeve of highly UV-C reflective material, the effective multiplier will increase. Using just 9 reflections to compare with the values for anodized aluminum and the same starting 100 photons the 9 reflections have 97, 94, 91, 89, 86, 83, 81, 78, 75 photons, respectively providing an effective multiplier of 8.75. Taking the number of reflections for the light to be reduced to the 27 of the anodized aluminum, with the coated/lined illumination chamber, it then takes 44 reflections to reduce the number of photons to 27, which results in a multiplier of 24.

The invention has been described in detail with particular reference to a presently preferred embodiment, but it will be understood that variations and modifications can be effected within the spirit and scope of the invention. The presently disclosed embodiments are therefore considered in all respects to be illustrative and not restrictive. The scope of the invention is indicated by the appended claims, and all changes that come within the meaning and range of equivalents thereof are intended to be embraced therein.

The invention claimed is:

1. An air flow system for reducing pathogens in a breathable airstream in an environment, the system comprising a device having:
   an airstream intake for receiving a volume of untreated air located at a first position;
   an airstream outlet for expelling a volume of treated air, the airstream outlet located at a second position extending above the first position;
   a flow path extending between the airstream intake and the airstream outlet;
   a UV-C source optically coupled to the flow path;
   an input power source operably connected to the UV-C source;
   an illumination channel along the flow path having a curvilinear UV-C highly reflective surface providing an optical effective power that exceeds the input power to the UV-C source; and
   a pressure generator fluidly connected to the airstream intake, the pressure generator configured to impart a flow from the airstream intake to the airstream outlet, wherein the pressure generator can be at least one of a force of flow provided by a pressurized source or a force of flow provided by a fan within a housing coupled to the illumination channel, wherein the illumination channel is configured to provide an exposure of at least 1.7 millijoules/cm$^3$ with an exposure time of less than 1 second resulting in a survival fraction with an MS2 pathogen of 0.52 or less.

2. The air flow system for reducing pathogens in a breathable airstream of claim 1, wherein the airstream intake is located on a first side of a support structure in the environment and the airstream outlet is located on a second side of the support structure in the environment, and wherein the airstream outlet further comprising a plurality of adjustable outlet ports to direct a flow of the volume of treated air towards at least one desired location.

3. The airflow system for reducing pathogens in a breathable airstream of claim 1, the airstream outlet further comprising a plurality of outlet ports disposed at a predetermined position to direct a flow of treated air towards a desired location.

4. The airflow system for reducing pathogens in a breathable airstream of claim 1, wherein the air flow system is in an indoor environment, and wherein the airflow system further comprises an air deflector spaced from the device and configured to change the flow of treated air from the airstream outlet of the device from a first direction to a second direction.

5. The airflow system for reducing pathogens in a breathable airstream of claim 4, wherein the shape of the air deflector includes a concave surface for interfacing with the flow of treated air from the airstream outlet.

6. The airflow system for reducing pathogens in a breathable airstream of claim 4, wherein the shape of the air deflector is selected from the group consisting of wedged, frusto-conical, pyramidal, elliptical, and linear.

7. The airflow system for reducing pathogens in a breathable airstream of claim 4, wherein the air deflector is mounted to or proximate a ceiling of a room.

8. The airflow system for reducing pathogens in a breathable airstream of claim 1, wherein the air flow system is in an indoor environment, and wherein the airstream intake for untreated air is generally positioned along a perimeter of the indoor environment.

9. The airflow system for reducing pathogens in a breathable airstream of claim 1, wherein the air flow system is in an indoor environment having a first fixed height, wherein a distance between the airstream intake located at the first position and the airstream outlet located at the second position forms a flow path length, and wherein a ratio of the flow path length to the first fixed height of the indoor environment is at or above 0.75.

10. The airflow system for reducing pathogens in a breathable airstream of claim 1, wherein the UV-C source is disposed within the illumination channel and includes a first radius and wherein the illumination channel is curvilinear and includes a second radius, the second radius being equal to or less than approximately 5 times the first radius UV-C source.

11. The airflow system for reducing pathogens in a breathable airstream of claim 1, wherein the air flow system is in an indoor environment having a first fixed height, and wherein the pressurized source providing a force of flow is an HVAC system fluidly connected to the airstream intake.

12. The airflow system for reducing pathogens in a breathable airstream of claim 11, wherein a distance between the airstream intake located at the first position and the airstream outlet located at the second position forms a flow path length, and wherein a ratio of the flow path length to the first fixed height of the indoor environment is at or above 0.75.

13. The apparatus for presenting treated air of claim 12, further comprising a plurality of the devices, wherein each device is spaced within an HVAC system.

14. The apparatus for presenting treated air of claim 13, wherein the treated air projected towards the central area moves generally downward in the central area.

15. The apparatus for presenting treated air of claim 14, wherein the treated air from one of the plurality of devices is generally maintained within a quarter of the indoor environment.

16. The airflow system for reducing pathogens in a breathable airstream of claim 1, wherein the illumination channel has a cross-sectional area in the range of 7,600 $mm^2$-7,800 $mm^2$.

17. The airflow system for reducing pathogens in a breathable airstream of claim 1, wherein the illumination channel provides a survival fraction with a COVID-19 pathogen of 0.5 or less.

18. The air flow system of claim 1, wherein the curvilinear UV-C highly reflective surface provides a gain of at least 5 times by reusing light produced by UV-C source optically coupled to the flow path.

19. The air flow system of claim 1, wherein a survival fraction of the system with an MS2 pathogen is in the range of 0.05 and 0.52.

20. The air flow system of claim 1, wherein the UV-C source has a first radius and wherein the illumination channel is curvilinear and has (i) a second radius and (ii) a cross-sectional area in the range of approximately 7,600 $mm^2$ and 18,000 $mm^2$; and (iii) a path length of approximately 1,200 mm to 1,600 mm, wherein the second radius of the illumination channel is equal to or less than approximately 5 times the radius of the UV-C source.

21. The air flow system of claim 1, wherein the air flow system is in an indoor environment and further comprises a plurality of the devices, wherein each device is spaced from an HVAC system, and wherein each device includes an air lens projecting an airstream treated by the device towards a central area within the indoor environment.

22. The air flow system of claim 21, wherein the treated airstream projected towards the central area moves generally downward in the central area.

23. The air flow system of claim 22, wherein the treated airstream from one of the plurality of devices is generally maintained within a quarter of the indoor environment.

24. An apparatus for presenting treated air, the apparatus comprising:
an elongate housing extending along a longitudinal axis, the elongate housing defining (i) an air intake extending along the longitudinal axis and located in a predetermined position, (ii) an air output port extending along the longitudinal axis, and (iii) an illumination channel having a curvilinear UV-C highly reflective surface and extending along the longitudinal axis, wherein the illumination channel is fluidly connected to the air intake and the air output port;
a pressure generator fluidly connected to the airstream intake and the air output port, the pressure generator configured to impart a flow from the air intake to the air output port; and
a UV-C source within the illumination channel, wherein untreated air flows from the air intake into the illumination channel, and then flows out of the air output port as treated air in a first direction, and wherein the curvilinear highly UV-C reflective surface of the illumination channel provides an optical effective power that exceeds the input power to the UV-C source, wherein the illumination channel is configured to provide an exposure of at least 1.7 millijoules/$cm^3$ with an exposure time of less than 1 second resulting in a survival fraction with an MS2 pathogen of 0.52 or less.

25. The apparatus for presenting treated air of claim 24, wherein the UV-C source is a pulse xenon lamp.

26. The apparatus for presenting treated air of claim 16, wherein the UV-C source is a mercury vapor lamp.

27. The apparatus for presenting treated air of claim 24, wherein the illumination channel comprises two sealingly engaged half-curvilinear channels.

28. The apparatus for presenting treated air of claim 24, wherein the curvilinear UV-C highly reflective surface provides a gain of at least 5 times by reusing light produced by the UV-C source within the illumination channel.

29. The apparatus for presenting treated air of claim 24, wherein a survival fraction of the apparatus with an MS2 pathogen is in the range of 0.05 and 0.52.

30. The apparatus for presenting treated air of claim 24, wherein the UV-C source has a first radius and wherein the illumination channel is curvilinear and includes (i) a second radius, (ii) a cross-sectional area in the range of approximately 7,600 $mm^2$ and 7,800 $mm^2$; and (iii) a path length of approximately 1200 mm to 1600 mm, wherein the second radius of the illumination channel is equal to or less than approximately 5 times the radius of the UV-C source.

* * * * *